United States Patent
Russel et al.

(10) Patent No.: US 11,788,119 B2
(45) Date of Patent: Oct. 17, 2023

(54) PADLOCK PROBE DETECTION METHOD

(71) Applicant: Q-linea AB, Uppsala (SE)

(72) Inventors: Camilla Russel, Uppsala (SE); Jenny Goransson, Uppsala (SE); Mats Gullberg, Sollentuna (SE)

(73) Assignee: Q-Linea AB, Uppsala (SE)

( * ) Notice: Subject to any disclaimer, the term of this patent is extended or adjusted under 35 U.S.C. 154(b) by 673 days.

(21) Appl. No.: 16/465,045

(22) PCT Filed: Dec. 15, 2017

(86) PCT No.: PCT/EP2017/083149
§ 371 (c)(1),
(2) Date: May 29, 2019

(87) PCT Pub. No.: WO2018/109206
PCT Pub. Date: Jun. 21, 2018

(65) Prior Publication Data
US 2020/0040376 A1     Feb. 6, 2020

(30) Foreign Application Priority Data
Dec. 16, 2016 (GB) .................................... 1621514

(51) Int. Cl.
*C12Q 1/682* (2018.01)
*C12Q 1/6853* (2018.01)

(52) U.S. Cl.
CPC ........... *C12Q 1/682* (2013.01); *C12Q 1/6853* (2013.01)

(58) Field of Classification Search
None
See application file for complete search history.

(56) References Cited

U.S. PATENT DOCUMENTS

| | | |
|---|---|---|
| 4,336,173 A | 6/1982 | Ugelstad |
| 5,714,320 A | 2/1998 | Kool |
| 5,854,033 A | 12/1998 | Lizardi |
| 5,989,823 A | 11/1999 | Jayasena et al. |
| 6,117,635 A | 9/2000 | Nazarenko et al. |
| 6,143,495 A | 11/2000 | Lizardi et al. |
| 6,183,960 B1 | 2/2001 | Lizardi |
| 6,248,526 B1 | 6/2001 | Weimer |
| 6,326,145 B1 | 12/2001 | Whitcombe et al. |
| 6,573,051 B2 | 6/2003 | Alsmadi et al. |
| 6,797,474 B2 | 9/2004 | Lizardi |
| 7,160,996 B1 | 1/2007 | Cook |
| 7,205,129 B1 | 4/2007 | Dean et al. |
| 7,320,860 B2 | 1/2008 | Landegren et al. |
| 2002/0064779 A1 | 5/2002 | Landegren et al. |
| 2003/0207295 A1 | 11/2003 | Gunderson et al. |
| 2004/0018491 A1 | 1/2004 | Gunderson et al. |
| 2004/0067511 A1 | 4/2004 | Thomas |
| 2009/0099041 A1 | 4/2009 | Church et al. |
| 2009/0233277 A1 | 9/2009 | Murakami |
| 2010/0028953 A1 | 2/2010 | Koch et al. |
| 2011/0183331 A1 | 7/2011 | Doi et al. |
| 2013/0288249 A1 | 10/2013 | Gullberg et al. |
| 2014/0357497 A1 | 12/2014 | Zhang et al. |
| 2015/0191773 A1 | 7/2015 | Viovy |

FOREIGN PATENT DOCUMENTS

| | | |
|---|---|---|
| CN | 102719550 A | 10/2012 |
| EP | 2 236 622 A2 | 10/2010 |
| WO | WO 95/22623 | 8/1995 |
| WO | WO 99/49079 | 9/1999 |
| WO | WO 01/61037 | 8/2001 |
| WO | WO 03/012119 A2 | 2/2003 |
| WO | WO 03/091406 A2 | 11/2003 |
| WO | WO 2005/111236 A1 | 11/2005 |
| WO | WO 2012/004931 A1 | 1/2012 |
| WO | WO 2012/152942 A1 | 11/2012 |
| WO | WO 2014/076214 A1 | 5/2014 |
| WO | WO 2015/071445 A1 | 5/2015 |
| WO | WO 2015/079042 A1 | 6/2015 |
| WO | WO 2015/083002 A2 | 6/2015 |

(Continued)

OTHER PUBLICATIONS

Akhras, Michael S. et al., "PathogenMip Assay: A Multiplex Pathogen Detection Assay", PLoS One, Issue 2, e223 (Feb. 2007), pp. 1-11.
Baner, Johan et al., "Parallel Gene Analysis With Allele-Specific Padlock Probes And Tag Microarrays", Nucleic Acids Research, vol. 31, No. 17, e103 (2003), pp. 1-7.
Dahl, Fredrik et al., "Circle-To-Circle Amplification For Precise And Sensitive DNA Analysis", PNAS, vol. 101, No. 13 (Mar. 30, 2004), pp. 4548-4553.
Goransson, Jenny et al., "Rapid Identification Of Bio-Molecules Applied For Detection Of Biosecurity Agents Using Rolling Circle Amplification", PLoS One, vol. 7, Issue 2, e31068 (Feb. 2012), pp. 1-9.
Hardenbol, Paul et al., "Multiplexed Genotyping With Sequence-Tagged Molecular Inversion Probes", Nature Biotechnology, vol. 21, No. 6 (Jun. 2003), pp. 673-678.

(Continued)

*Primary Examiner* — Samuel C Woolwine
*Assistant Examiner* — Carolyn L Greene
(74) *Attorney, Agent, or Firm* — Lippes Mathias LLP

(57) ABSTRACT

Multiplexed methods of detecting an analyte in a sample using two or more padlock probes each specific to a different target sequence are described. The target sequence is either part of an analyte or indicative of the presence of an analyte in the sample. Each padlock probe includes an analyte-specific reporter sequence, and either a restriction cleavage site located 3' of the analyte-specific reporter sequence, and/or a first amplification primer binding site for an amplification reaction. Where the padlock probe includes a restriction cleavage site, cleavage at the restriction cleavage site occurs 3' of the analyte-specific reporter sequence. Where the padlock probe includes a first amplification primer binding site for the further amplification reaction, it does not contain a second amplification primer binding site 5' of the analyte-specific reporter sequence. Panels of probes and kits for the same are also described.

19 Claims, 7 Drawing Sheets

Specification includes a Sequence Listing.

(56) References Cited

FOREIGN PATENT DOCUMENTS

| WO | WO 2015/189390 A1 | 12/2015 |
|---|---|---|
| WO | WO 2016/053638 A1 | 4/2016 |

OTHER PUBLICATIONS

Heid, Christian A. et al., "Real Time Quantitative PCR", Genome Research, 6, (Oct. 1996), pp. 986-994.

Holland, Pamela M. et al., "Detection Of Specific Polymerase Chain Reaction Product By Utilizing the 5'→3' Exonuclease Activity of *Thermus Aquaticus* DNA Polymerase", Proc. Natl. Acad. Sci. USA, vol. 88 (Aug. 1991) pp. 7276-7280.

Kühnemund, Malte et al., "Circle-to-Circle Amplification on a Digital Microfluidic Chip For Amplified Single Molecule Detection", Lab Chip. (2014) 14, pp. 2983-2992.

Lee, Linda G. et al., "Allelic Discrimination by Nick-Translation PCR With Fluorogenic Probes", Nucleic Acids Research (1993) vol. 21, No. 16, pp. 3761-3766.

Marciniak, Jennifer Y. et al., "Coupled Rolling Circle Amplification Loop-Mediated Amplification For Rapid Detection of Short DNA Sequences", BioTechniques, vol. 45, No. 3 (Sep. 2008) pp. 275-280.

Mezger, Anja et al., "A General Method For Rapid Determination of Antibiotic Susceptibility and Species in Bacterial Infections", Journal of Clinical Microbiology, vol. 53, No. 2 (Feb. 2015) pp. 425-432.

Nazarenko, I. A. et al., "A Closed Tube Format For Amplification and Detection of DNA Based on Energy Transfer", Nucleic Acids Research, vol. 25, No. 12 (1997) pp. 2516-2521.

Smith, James H. et al., "Detection of Nucleic Acid Targets Using Ramified Rolling Circle DNA Amplification: A Single Nucleotide Polymorphism Assay Model", PloS One, vol. 8, Issue 5 (May 2013) e65053, pp. 1-8.

Tyagi, Sanjay et al., "Molecular Beacons: Probes That Fluoresce Upon Hybridization", Nature Biotechnology, vol. 14 (Mar. 1996) pp. 303-308.

Wang, Xingyu et al., "Highly Specific DNA Detection From Massive Background Nucleic Acids Based on Rolling Circle Amplification of Target dsDNA", RSC Adv. (2014) 4, pp. 38293-38299.

Whitcombe, David et al., "Detection of PCR Products Using Self-Probing Amplicons and Fluorescence", Nature Biotechnology, vol. 17 (Aug. 1999) pp. 804-807.

International Search Report/Written Opinion of International Application No. PCT/EP2017/083149 dated Apr. 3, 2018, 14 pages.

United Kingdom International Patent Office Search Report of British Application No. GB1621514.7 dated Oct. 27, 2017, 1 page.

Figure 1
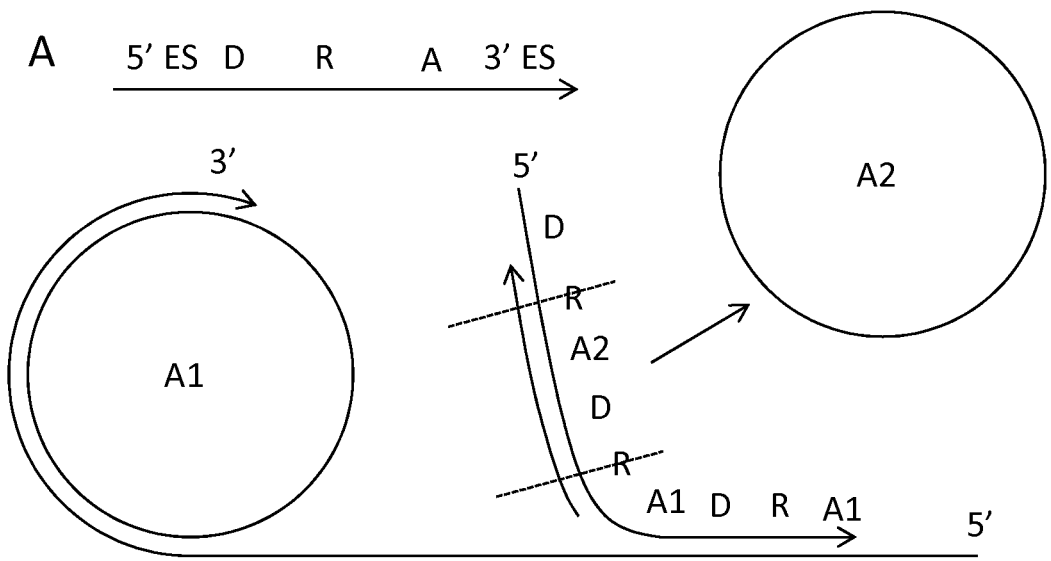
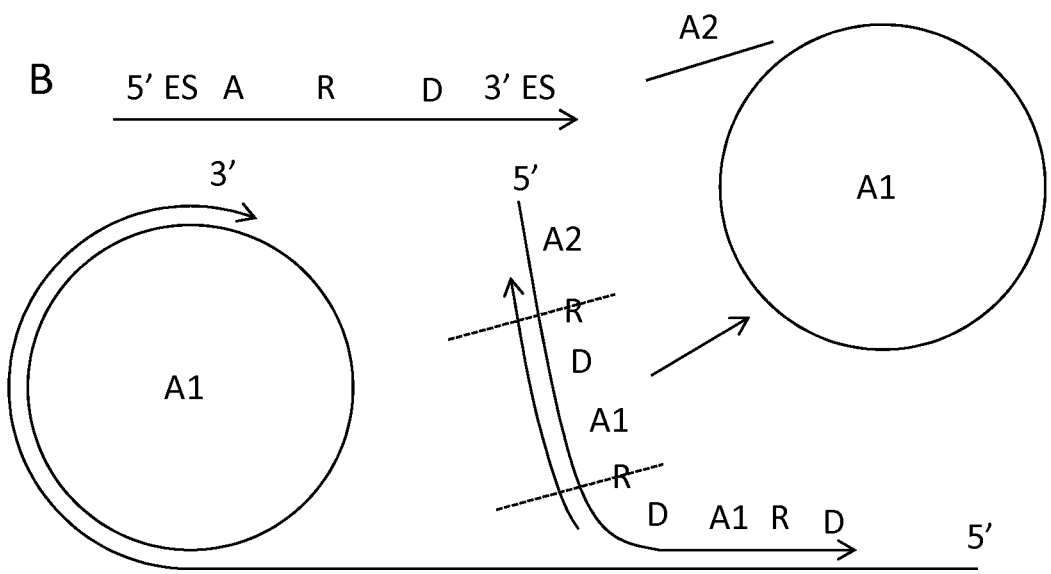

Figure 2
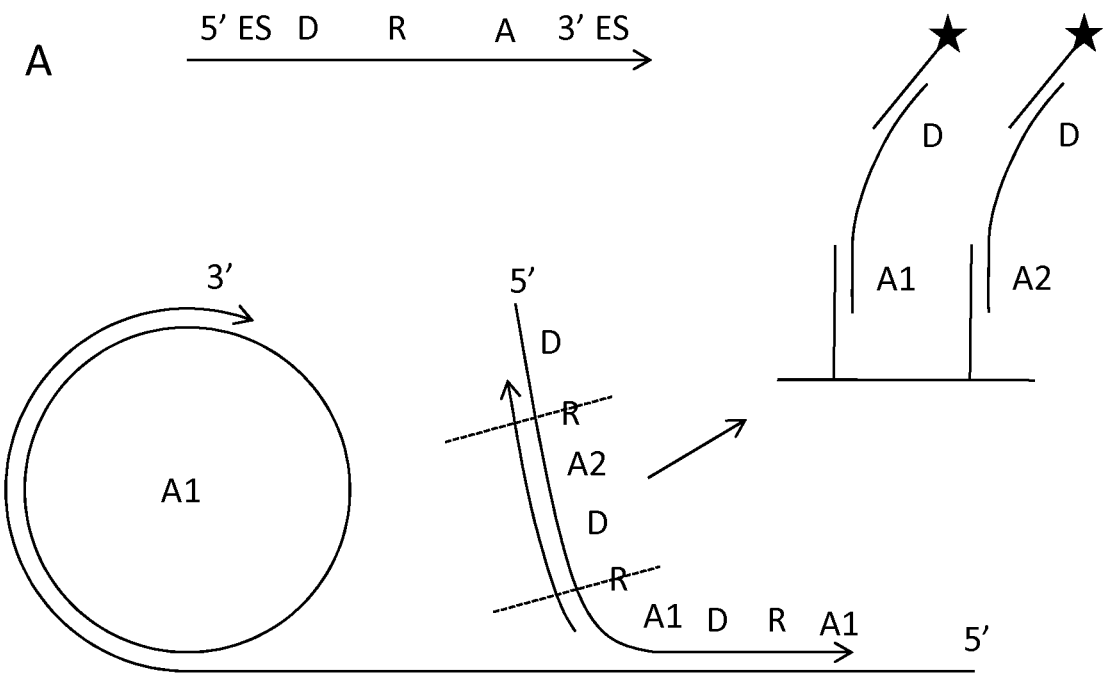
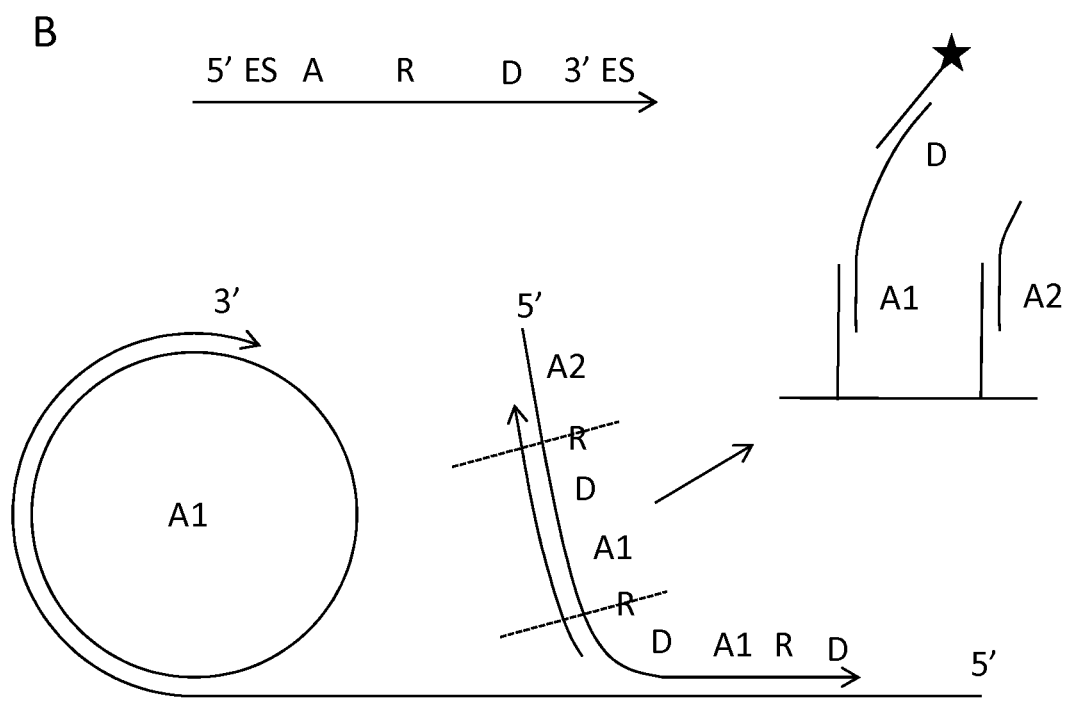

Figure 6
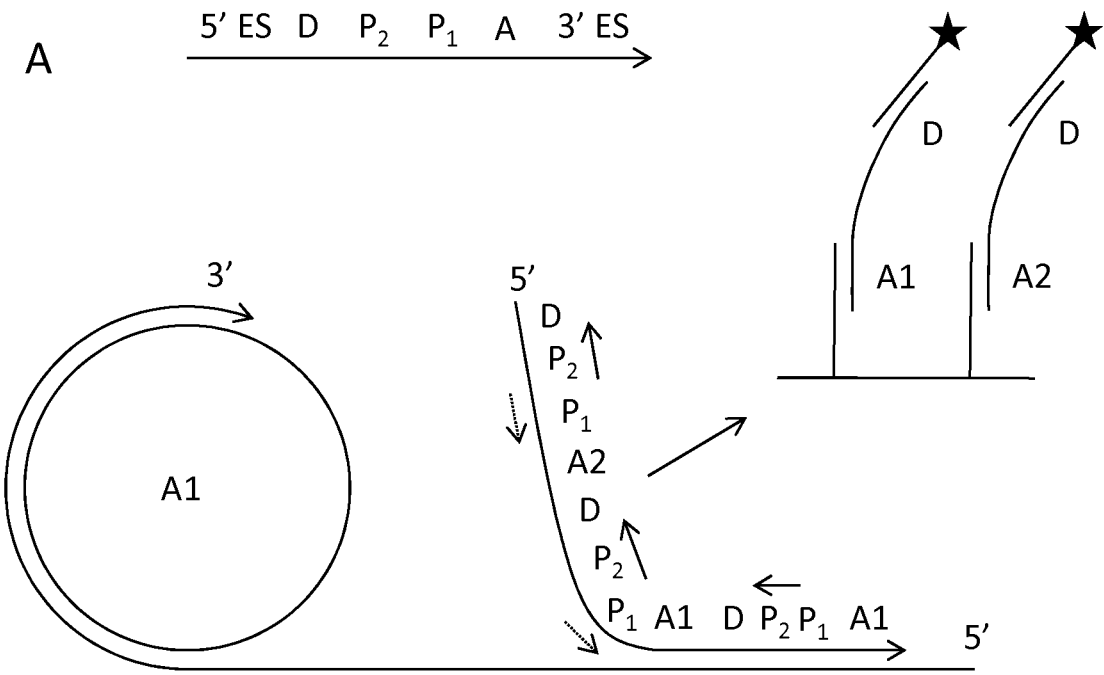
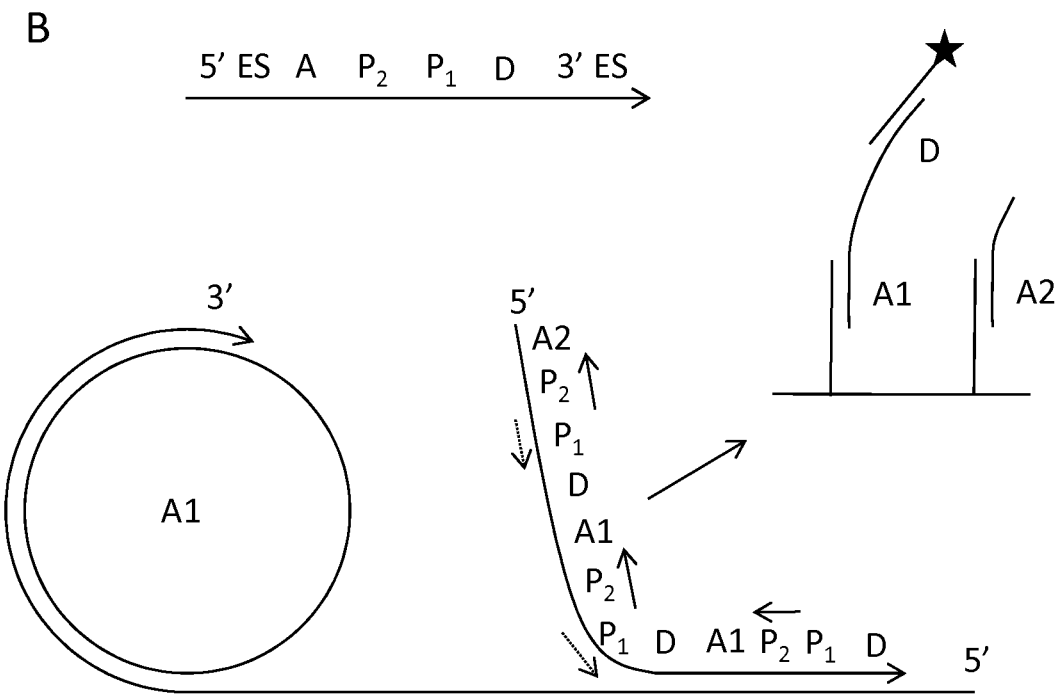

SEQUENCE LISTING

<160> NUMBER OF SEQ ID NOS: 21

<210> SEQ ID NO 1
<211> LENGTH: 93
<212> TYPE: DNA
<213> ORGANISM: Artificial Sequence
<220> FEATURE:
<223> OTHER INFORMATION: Padlock probe
<220> FEATURE:
<221> NAME/KEY: modified_base
<222> LOCATION: (1)..(1)
<223> OTHER INFORMATION: 5' Phosphate

<400> SEQUENCE: 1
cctggaactg gctggtgcgt ctatttagtg gagccgacag accagctatc gtcgtaacct    60
agtcgaggcg cttcaagagt gggaagcgaa aat    93

<210> SEQ ID NO 2

```
<211> LENGTH: 93
<212> TYPE: DNA
<213> ORGANISM: Artificial Sequence
<220> FEATURE:
<223> OTHER INFORMATION: Padlock probe
<220> FEATURE:
<221> NAME/KEY: modified_base
<222> LOCATION: (1)..(1)
<223> OTHER INFORMATION: 5' Phosphate

<400> SEQUENCE: 2
cctggaactg gctggggatc tcacgttctc tggattgcgt ctatttagtg gagccgacag    60
accagctatc gtcgtagagt gggaagcgaa aat                                 93

<210> SEQ ID NO 3
<211> LENGTH: 70
<212> TYPE: DNA
<213> ORGANISM: Artificial Sequence
<220> FEATURE:
<223> OTHER INFORMATION: Padlock probe
<220> FEATURE:
<221> NAME/KEY: modified_base
<222> LOCATION: (1)..(1)
<223> OTHER INFORMATION: 5' Phosphate

<400> SEQUENCE: 3
aggtcgttag aaagcccgct gctaacaatg tgtcaacgac agaccagcta tcgtcgtgga    60
cctaaacctc                                                           70

<210> SEQ ID NO 4
<211> LENGTH: 97
<212> TYPE: DNA
<213> ORGANISM: Artificial Sequence
<220> FEATURE:
<223> OTHER INFORMATION: QP-676 Probe C-8 (pos)
<220> FEATURE:
<221> NAME/KEY: modified_base
<222> LOCATION: (1)..(1)
<223> OTHER INFORMATION: 5' Phosphate

<400> SEQUENCE: 4
agatcacgag cacagaaatg cgtctattta gtggagccga cagaccagct atcgtcgtat    60
acagtggcag tagcacgacg ataaacctat cgaccct                             97

<210> SEQ ID NO 5
<211> LENGTH: 99
<212> TYPE: DNA
<213> ORGANISM: Artificial Sequence
<220> FEATURE:
<223> OTHER INFORMATION: QP-662 Probe target 1
<220> FEATURE:
<221> NAME/KEY: modified_base
<222> LOCATION: (1)..(1)
<223> OTHER INFORMATION: 5' Phosphate

<400> SEQUENCE: 5
catacgacat cgttgatcat gcgtctattt agtggagccg acagaccagc tatcgtcgtt    60
aaggccctgc actgctgtac aatcagactt acactagcc                           99

<210> SEQ ID NO 6
<211> LENGTH: 96
<212> TYPE: DNA
<213> ORGANISM: Artificial Sequence
<220> FEATURE:
<223> OTHER INFORMATION: QP 663 Probe target2
<220> FEATURE:
<221> NAME/KEY: modified_base
```

```
<222> LOCATION: (1)..(1)
<223> OTHER INFORMATION: 5' Phosphate

<400> SEQUENCE: 6
gggaacggtt cttgggtgcg tctatttagt ggagccgaca gaccagctat cgtcgttaag    60
gccctgcact gctgtatagg cttaaaggcc tagtaa                              96

<210> SEQ ID NO 7
<211> LENGTH: 92
<212> TYPE: DNA
<213> ORGANISM: Artificial Sequence
<220> FEATURE:
<223> OTHER INFORMATION: QP-739 Probe target 2
<220> FEATURE:
<221> NAME/KEY: modified_base
<222> LOCATION: (1)..(1)
<223> OTHER INFORMATION: 5' Phosphate

<400> SEQUENCE: 7
cgccagtttc gagtgatgcg tctatttagt ggagccgaca gaccagctat cgtcgttcgt    60
acagagattg acctgcgcct atgacctcgg ga                                  92

<210> SEQ ID NO 8
<211> LENGTH: 89
<212> TYPE: DNA
<213> ORGANISM: Artificial Sequence
<220> FEATURE:
<223> OTHER INFORMATION: QP-740 Probe target 2
<220> FEATURE:
<221> NAME/KEY: modified_base
<222> LOCATION: (1)..(1)
<223> OTHER INFORMATION: 5' Phosphate

<400> SEQUENCE: 8
atggtcagcc gcagttgcgt ctatttagtg gagccgacag accagctatc gtcgttcgta    60
cagagattga cctgcagggg cgctgactt                                      89

<210> SEQ ID NO 9
<211> LENGTH: 94
<212> TYPE: DNA
<213> ORGANISM: Artificial Sequence
<220> FEATURE:
<223> OTHER INFORMATION: QP-741 Probe target 2
<220> FEATURE:
<221> NAME/KEY: modified_base
<222> LOCATION: (1)..(1)
<223> OTHER INFORMATION: 5' Phosphate

<400> SEQUENCE: 9
ggatccaaca cctagcatgc gtctatttag tggagccgac agaccagcta tcgtcgttcg    60
tacagagatt gacctgcgca ctgaatcccg gaaa                                94

<210> SEQ ID NO 10
<211> LENGTH: 20
<212> TYPE: DNA
<213> ORGANISM: Artificial Sequence
<220> FEATURE:
<223> OTHER INFORMATION: Q-2132 Primer +

<400> SEQUENCE: 10
gacagaccag ctatcgtcgt                                                20

<210> SEQ ID NO 11
<211> LENGTH: 20
<212> TYPE: DNA
```

```
<213> ORGANISM: Artificial Sequence
<220> FEATURE:
<223> OTHER INFORMATION: Q-2282 Primer -

<400> SEQUENCE: 11
ggctccacta aatagacgca                                                   20

<210> SEQ ID NO 12
<211> LENGTH: 99
<212> TYPE: DNA
<213> ORGANISM: Artificial Sequence
<220> FEATURE:
<223> OTHER INFORMATION: QP-1160 Probe target 1

<400> SEQUENCE: 12
catacgacat cgttgatcat aaggccctgc actgctgtag acagaccagc tatcgtcgtt       60
gcgtctattt agtggagccc aatcagactt acactagcc                              99

<210> SEQ ID NO 13
<211> LENGTH: 96
<212> TYPE: DNA
<213> ORGANISM: Artificial Sequence
<220> FEATURE:
<223> OTHER INFORMATION: QP-1161 Probe target 1
<220> FEATURE:
<221> NAME/KEY: modified_base
<222> LOCATION: (1)..(1)
<223> OTHER INFORMATION: 5' Phosphate

<400> SEQUENCE: 13
gggaacggtt cttgggtaag gccctgcact gctgtagaca gaccagctat cgtcgttgcg       60
tctatttagt ggagcctagg cttaaaggcc tagtaa                                 96

<210> SEQ ID NO 14
<211> LENGTH: 92
<212> TYPE: DNA
<213> ORGANISM: Artificial Sequence
<220> FEATURE:
<223> OTHER INFORMATION: QP-1162 Probe target 2
<220> FEATURE:
<221> NAME/KEY: modified_base
<222> LOCATION: (1)..(1)
<223> OTHER INFORMATION: 5' Phosphate

<400> SEQUENCE: 14
cgccagtttc gagtgatcgt acagagattg acctgcgaca gaccagctat cgtcgttgcg       60
tctatttagt ggagccgcct atgacctcgg ga                                     92

<210> SEQ ID NO 15
<211> LENGTH: 89
<212> TYPE: DNA
<213> ORGANISM: Artificial Sequence
<220> FEATURE:
<223> OTHER INFORMATION: QP-1162 Probe target 2
<220> FEATURE:
<221> NAME/KEY: modified_base
<222> LOCATION: (1)..(1)
<223> OTHER INFORMATION: 5' Phosphate

<400> SEQUENCE: 15
atggtcagcc gcagttcgta cagagattga cctgcgacag accagctatc gtcgttgcgt       60
ctatttagtg gagccagggg cgctgactt                                         89

<210> SEQ ID NO 16
<211> LENGTH: 94
```

-continued

```
<212> TYPE: DNA
<213> ORGANISM: Artificial Sequence
<220> FEATURE:
<223> OTHER INFORMATION: QP-1164 Probe target 2
<220> FEATURE:
<221> NAME/KEY: modified_base
<222> LOCATION: (1)..(1)
<223> OTHER INFORMATION: 5' Phosphate

<400> SEQUENCE: 16
ggatccaaca cctagcatcg tacagagatt gacctgcgac agaccagcta tcgtcgttgc      60
gtctatttag tggagccgca ctgaatcccg gaaa                                 94

<210> SEQ ID NO 17
<211> LENGTH: 97
<212> TYPE: DNA
<213> ORGANISM: Artificial Sequence
<220> FEATURE:
<223> OTHER INFORMATION: QP-1166 Probe C-8 (Pos)
<220> FEATURE:
<221> NAME/KEY: modified_base
<222> LOCATION: (1)..(1)
<223> OTHER INFORMATION: 5' Phosphate

<400> SEQUENCE: 17
agatcacgag cacagaaaat acagtggcag tagcacgaga cagaccagct atcgtcgttg      60
cgtctattta gtggagcccg ataaacctat cgaccct                              97

<210> SEQ ID NO 18
<211> LENGTH: 20
<212> TYPE: DNA
<213> ORGANISM: Artificial Sequence
<220> FEATURE:
<223> OTHER INFORMATION: Q-2131 Primer -

<400> SEQUENCE: 18
acgacgatag ctggtctgtc                                                 20

<210> SEQ ID NO 19
<211> LENGTH: 20
<212> TYPE: DNA
<213> ORGANISM: Artificial Sequence
<220> FEATURE:
<223> OTHER INFORMATION: Q-2281 Primer +

<400> SEQUENCE: 19
tgcgtctatt tagtggagcc                                                 20

<210> SEQ ID NO 20
<211> LENGTH: 20
<212> TYPE: DNA
<213> ORGANISM: Artificial Sequence
<220> FEATURE:
<223> OTHER INFORMATION: Q-1599 Detection
<220> FEATURE:
<221> NAME/KEY: modified_base
<222> LOCATION: (1)..(1)
<223> OTHER INFORMATION: 5' Cy3

<400> SEQUENCE: 20
tgcgtctatt tagtggagcc                                                 20

<210> SEQ ID NO 21
<211> LENGTH: 100
<212> TYPE: DNA
<213> ORGANISM: Artificial Sequence
<220> FEATURE:
```

```
<223> OTHER INFORMATION: Q-1064 Template
<220> FEATURE:
<221> NAME/KEY: modified_base
<222> LOCATION: (1)..(1)
<223> OTHER INFORMATION: 5' Phosphate

<400> SEQUENCE: 21
tttgaggaaa cccgtcctcc cgtctatttc gctcctcata tcgttccagc gcttttagca        60
cgtttctgtg ctcgtgatct agggtcgata ggtttatcgc                            100
```

PADLOCK PROBE DETECTION METHOD

This application claims the priority of International Application PCT/EP2017/083149, filed Dec. 15, 2017, and GB1621514.7, filed Dec. 16, 2016, from which the PCT application claims priority, the disclosures of which are incorporated herein by reference in their entireties.

BACKGROUND

The present invention lies in the field of analyte detection by rolling circle amplification (RCA), and relates specifically to an improved method of detecting an analyte in a sample using padlock probes.

Rolling circle replication (RCR) is a mechanism used in nature for the replication of circular DNA molecules such as plasmids or viruses. The reaction has been adopted as the basis for a laboratory method for amplifying circular molecules and, as well as having utility in methods of amplifying or producing nucleic acids, has been demonstrated to be useful in a variety of assays which use or generate a circular nucleic acid molecule as a reporter; in such assay methods the circular molecule is amplified (replicated) by RCA and the replicated or amplified circular nucleic acid molecule is detected. In other methods, desired, or target molecules may be circularized and amplified by RCA. Accordingly, rolling circle replication (RCR) is now commonly referred to as rolling circle amplification (RCA), and these terms are used interchangeably herein.

RCA relates to the synthesis of nucleic acid molecules using a circular single stranded nucleic acid molecule, e.g. an oligonucleotide, as RCA template and a strand-displacing polymerase to extend a primer which is hybridized to the circular template (the strand displacing activity displaces the primer and effectively causes the circle to "roll"). The primer may in certain typical assays be provided by a target nucleic acid (RNA or DNA) molecule. The addition of a polymerase and nucleotides starts the synthesis reaction, i.e. polymerization. As the RCA template is endless, the resultant product is a long single stranded nucleic acid molecule composed of tandem repeats, or monomers, that are complementary to the RCA template (i.e. a concatemer). This linear amplification of the circular RCA template is the first (and in some instances the only) step of a RCA reaction—as will be described in more detail below, RCA reactions may include further or additional steps or reactions, such as extension reactions templated by the first RCA product (herein termed a RCP), as occurs in hyperbranched RCA (HRCA) for example.

Circles (circular templates) for RCA reactions may be formed or provided in various ways, for example they may be provided as reporter molecules, formed from probes which are circularized as part of a detection reaction (e.g. padlock probes the ends of which are directly or indirectly ligated upon hybridization to a target molecule to form a circularized molecule), target molecules for isolation or detection may be circularized, or substrates for amplification may be circularized or incorporated into circular nucleic acid molecules, for example by ligating or hybridizing adaptors for circularization to the ends of the target or substrate molecules.

A concatemeric RCA product may be detected in homogenous ("in solution") or heterogeneous (solid phase-based) assays. For instance, a RCA reaction may result in a 1000-fold amplification of the circle in just 1 hour (based on a circle consisting of about 100 nucleotides). Thus, the RCA of a circular oligonucleotide may result in a RCA product that forms a bundle or "blob" of DNA that can be about 1 µm in diameter. The product, i.e. blob, may be visualized, for example detected by labelling, e.g. by the hybridization of nucleic acid probes conjugated to fluorescent (or other) labels which allows the blob to be visualized by (fluorescence) microscopy or flow cytometry. In other embodiments, RCA products may be reduced to monomers by digestion with a restriction enzyme or a ribozyme, which are then detected. The RCA product or monomers derived therefrom may be detected and/or analyzed by sequencing or other sequence analysis procedures, or may be detected by other means e.g. by an array-based readout.

Due to the ability of the RCA reaction to generate a readily detectable signal it is useful as a reporter system for detection of any nucleic acid molecule in a sample, which may be a target nucleic acid molecule (i.e. a nucleic acid molecule to be detected, or where the nucleic acid molecule is the "analyte" of the assay), or it may be a nucleic acid molecule which is to be detected as a marker (or proxy) for the presence of the target analyte (i.e. as a nucleic acid sequence which is indicative of the presence of the "analyte" of the assay). RCA has thus also been utilized in methods for the detection of other analytes, i.e. analytes other than nucleic acid molecules, such as proteins, peptides etc. In this respect, a variety of assays have been developed in which a nucleic acid molecule may be used to directly or indirectly tag or label a target analyte in a sample and detection of the nucleic acid molecule serves to indicate the presence of the analyte in the sample. In some methods a new nucleic acid molecule may be generated in a sample (i.e. a nucleic acid molecule that was not present in the original sample and was not one of the components added to the sample) when one or more molecules interact with, e.g. bind to, the target analyte. The detection of the generated nucleic acid molecule is indicative of the analyte in a sample.

Various methods based upon detecting such a proxy or marker nucleic acid molecule using an RCA reaction as part of the detection strategy are well described in the art, including for example, immuno-RCA, assays using padlock probes and proximity probe assays which generate a circular nucleic acid molecule. In all these cases, the methods rely on providing or generating a circular nucleic acid molecule which may then be used as a substrate (template) for a RCA reaction, and the RCA product may then be detected as a substitute for detecting the target analyte directly.

For example a proximity assay is described by Landegren et al. in WO 99/49079. In such a method the ends of the added linear oligonucleotide(s) are brought into juxtaposition for ligation to form a circular template for RCA by hybridizing to one or more circularization templates provided by the nucleic acid domain of one or more proximity probes. Various such assay formats are described in WO 01/61037.

It will accordingly be evident that RCA may be of utility in the specific detection of any nucleic acid molecule in a sample, regardless of whether it is the "original" (or actual) target analyte in a sample or it is a "proxy" for the target analyte generated by the interaction of specific detection molecules, e.g. proximity probes, with the target analyte, e.g. protein. RCA may also be useful in the detection of amplified nucleic acid molecules. For instance, in samples in which the target nucleic acid molecule is present in low amounts, e.g. rare transcripts, RCA can be used to "enhance" detection by increasing the amount of nucleic acid that is available to be detected. RCA has proved to be particularly useful for parallel amplification of many nucleic acid molecules simultaneously, and to generate un-skewed amplification of multiple sequences i.e. it is particularly useful in multiplex contexts (see for example, WO 03/012119, WO 99/49079 and WO 2005/111236).

Despite the utility of RCA as a method for detecting an analyte in a sample, there are certain drawbacks associated with RCA, and various proposed solutions have been developed in order to improve the efficiency of replication and analyte detection.

Unlike PCR, a simple RCA reaction (i.e. the first step as described above) is a linear process and accordingly amplification of the RCA template is relatively slow relative to exponential amplification methods. In order to increase the amount or rate of amplification various modifications of the basic RCA reaction have been proposed, including to provide a more than linear amplification, for example to improve sensitivity in assays based upon detecting an RCA product. Thus for example hyperbranched RCA (HBRCA/HRCA) has been developed (U.S. Pat. Nos. 6,183,960 and 6,143,495). HRCA may however result in an uncontrolled and variable amount of amplified product being produced and may be prone to false starts. Furthermore double-stranded product is produced in this reaction and it may in many cases be desirable to have a single-stranded nucleic acid molecule, e.g. for downstream detection.

In WO 03/012199 a method, termed the circle-to-circle amplification (C2CA) method, based on repeat RCA reactions, is described, which may be used for amplifying the product generated from a first RCA reaction. In this method the first generation RCA product (generated from a first "circle" or circular RCA template) is cleaved into monomers (for example each monomer corresponding to one tandem repeat in the concatemeric product), which are circularized and then used as RCA templates (i.e. as second circles or circular templates) in a further round of RCA. Cleavage may be achieved by hybridizing an oligonucleotide to a sequence (restriction site sequence) present in each repeat (monomer) of the RCA product to create a double-stranded restriction cleavage or recognition site and cleaving with a restriction enzyme to cleave the product into monomers.

In the methods described in WO2015/079042, the efficiency of the C2CA method is improved by speeding up the "second" or subsequent RCA reaction. This is achieved by reducing the size of the "second" RCA template and only selecting and circularizing a part (or parts) of each monomer repeat of the first RCA product. Thus, the successive (i.e. "second") RCA reaction may be performed using a shorter circular RCA template than the first generation RCA which produced the first RCA product (RCP). Since the rate of RCP production (i.e. the rate at which the RCA template is replicated) is dependent on size of the RCA template, the shorter the circle, the faster amplification may take place. In this way, the rate of RCA amplification using C2CA may be enhanced.

RCA is also known to be prone to relatively high levels of background signal arising from a number of different sources, including incorrect (non-specific) formation of RCA templates and/or priming of RCA itself, and non-specific binding of nucleic acid molecules present in the sample, or reaction mixture, to the RCP, resulting in the priming an extension reaction using the RCA product as an extension template. This is exacerbated when multiple analytes are to be detected by RCA in multiplex method, and such problems are compounded when any of the above-mentioned methods for enhancing amplification of the RCP are used, as any non-specific RCP that is generated may be amplified and thus increased.

Levels of background signal may be reduced by use of padlock probes to generate the RCA template. Padlock probes are circularizable oligonucleotides which have target-specific regions at their 5' and 3' ends, such that formation of the RCA template is target-dependent, as this requires double recognition of the target (which may be the analyte or a proxy for the analyte) for an RCA template to be formed. Only when both the target-specific "binding domains" at both ends of the padlock probe have bound to their respective, complementary binding sites in the target nucleic acid molecule, can the ends be ligated together, directly when the ends have hybridized adjacent to one another, or indirectly when they have hybridized with a gap between them, to form a circular RCA template. When the ends have hybridized to leave a gap, this may be filled either by a "gap-filling" oligonucleotide which hybridizes in-between and the ends of which are ligated to the respective 5' and 3' ends of the padlock probe, or by extending the hybridized 3' end of the padlock probe before ligation to the 5' end. Further improvements are also achievable: circularization of a padlock probe results in the probe becoming catenated with the analyte, and thus immobilization of the analyte and subsequent washing steps can remove any unbound (and thus non-circularized) padlock probes from the sample. Furthermore, careful selection of the annealing conditions for probe hybridization or the ligation conditions (e.g. the temperature at which ligation may take place, and/or fine-tuning the sequences of the padlock probes which may bind to the analyte) may also help reduce the background signal associated with RCA. Other methods for this are described e.g. in U.S. Pat. No. 5,854,033, and include the use of a specific ligase, exonuclease degradation of linear padlock probes, PNA clamps, gap-fill circularization, and use of specific ligase enzymes.

Various other probe designs have also been proposed to reduce the target-independent signal generated in RCA, e.g. as in WO2014/076214 and WO2012/152942. However, the complexity and costs associated with the manufacture and use of such probe designs may limit their use, and thus for many applications, padlock probes remain the design of choice in many RCA-based methods.

Despite the improvements that have been made to improve the detection limit of RCA (and in particular, of RCA which utilises a padlock probe to detect an analyte), there remains a need for advances to further reduce the background signal generated in an RCA, and thus to further lower the detection limit of RCA. In particular there is a need to reduce unwanted, non-specifically primed extension reactions which use a RCA product (RCP) as template for the extension reaction, that is extension reactions primed by the non-specific (i.e. off-target) hybridization of nucleic acid molecules to a RCP. Unwanted extension products generated in this way may themselves serve as templates for further unwanted extension reactions and accordingly, in effect represent an unwanted HRCA reaction, leading to amplification of unwanted extension products. Molecules which may act as primers when non-specifically hybridized include unreacted probes, e.g. non-specifically bound padlock probes.

Thus, it has been observed that linear nucleic acid molecules, including oligonucleotides which may be present in the sample or reaction mixture, (e.g. non-circularized padlock probes) are capable of binding to an RCP formed on the detection of an analyte in a sample, and priming an extension reaction using the RCP as an extension template. This is of particular concern in multiplexed detection methods using two or more padlock probes, where each probe comprises a reporter (e.g. tag) sequence indicative of the presence of the analyte, as a non-target specific padlock probe (comprising a reporter sequence indicative of the presence of an 'incorrect' analyte (i.e. the "wrong" analyte, or a different analyte to that detected by the padlock probe which templated the RCP)) may bind to the RCP (i.e. non-specific or off-target hybridization), and prime an extension reaction. Padlock probes used in prior art multiplexed detection methods (e.g. as described in Banér et al. 2003. Nucleic Acids Research 13, e103) typically comprise such tag sequences towards their 3' ends, and thus such non-specific binding of a padlock probe to the RCP results in the incorporation of the 'incorrect' reporter sequence at the 5' end of the resulting extension (i.e. a reporter sequence which is indicative of the presence of an analyte other than the analyte which was detected by the padlock probe which was circularized to form the original (first) RCA template). This non-target specific reporter sequence may subsequently be detected, or more problematically amplified and detected, and would thus be indicative of the presence of the incorrect analyte in the sample (i.e. a false-positive signal for that analyte). This is therefore a significant source of background signal in a multiplexed RCA-based detection assay.

BRIEF DESCRIPTION

A multiplexed method of detecting an analyte in a sample using two or more padlock probes each specific to a different target sequence is described. The target sequence is either part of an analyte or indicative of the presence of an analyte in the sample. The method includes contacting the sample with the two or more padlock probes and allowing the probes to hybridize to their respective target sequences, if present. Any padlock probe which has hybridized to its target nucleic acid sequence is circularized by ligation to form a rolling circle amplification (RCA) template. Ligated padlock probes are amplified by performing at least a linear RCA reaction, using the RCA template(s) previously formed, to form first rolling circle amplification product(s) (RCP). A first of the RCP is a concatemer including monomers which are complementary to the circularized padlock probe which templated its formation. Optionally, simultaneously with or subsequently to the linear RCA reaction, a further amplification reaction is performing to amplify the first RCP(s). Optionally, during or after the amplifying of ligated padlock probes, a restriction cleavage step is performed. The method further includes detecting the amplification product(s) to detect the analyte(s). Each of the padlock probes includes 5' and 3' end sequences that are capable of hybridizing to a different target nucleic acid sequence, such that upon hybridization, the ends of the padlock probe are brought into juxtaposition, directly or indirectly, for ligation to circularize the padlock probe and between the said 5' and 3' end sequences: at least one reporter sequence and a restriction oligonucleotide (RO) sequence. At least one of the reporter sequences is an analyte-specific reporter sequence. The RO sequence is capable of hybridizing to a complementary sequence to create a restriction cleavage site. The RO sequence is located 3' of the analyte-specific reporter sequence, and/or a first amplification primer binding site for a further amplification reaction. Where the padlock probe includes the RO sequence, the restriction cleavage of step (d) uses a restriction enzyme capable of cleaving the restriction cleavage site, optionally together with a restriction oligonucleotide which is complementary to and capable of hybridizing to the restriction oligonucleotide (RO) sequence. Cleavage at the restriction cleavage site occurs 3' of the analyte-specific reporter sequence. Where the padlock probe includes the first amplification primer binding site for the further amplification reaction, it does not contain a second amplification primer binding site 5' of the analyte-specific reporter sequence.

A panel of padlock probes for use in multiplexed detection of an analyte in a sample is also described. The panel includes at least two padlock probes, wherein each padlock probe comprises 5' and 3' end sequences capable of hybridizing to a different target nucleic acid sequence, which target sequence is either part of the analyte or is indicative of the presence of the analyte in the sample, such that upon such hybridization the ends of the padlock probe are brought into juxtaposition, directly or indirectly, for ligation to circularize the padlock probe. Each padlock probe includes, between its 5' and 3' ends, at least one reporter sequence. At least one of the reporter sequences is an analyte-specific reporter sequence and one or both of (i) a restriction oligonucleotide (RO) sequence capable of hybridizing to a complementary sequence to create a restriction cleavage site, wherein the RO sequence is located 3' of the analyte-specific reporter sequence such that cleavage at the restriction cleavage site occurs 3' of the analyte-specific reporter sequence and allows the analyte-specific reporter sequence to be removed from the padlock probe, or (ii) a binding site for a first amplification primer, wherein the binding site may be present 5' of, 3' of, or within the analyte-specific reporter sequence. Where the first amplification primer binding site is present, the padlock probe does not comprise a binding site for a second amplification primer 5' of the analyte-specific reporter sequence.

BRIEF DESCRIPTION OF THE DRAWINGS

FIGS. 1A and 1B are schematics illustrating different padlock probes, each including 5' and 3' target-specific end sequences an array oligonucleotide sequence (A), and a detection oligonucleotide sequence (D);

FIG. 2A illustrates a detection oligonucleotide sequence deriving from an unligated padlock probe, being 3' to a restriction oligonucleotide sequence and FIG. 2B illustrates a detection oligonucleotide sequence deriving from an unligated padlock probe, being within the restriction oligonucleotide sequence;

FIGS. 6A and 6B are schematics illustrating different padlock probes including 5' and 3' target-specific end sequences (5' ES and 3' ES), analyte-specific reporter sequences (A), first and second primer binding sites ($P_1$ and $P_2$) and detection oligonucleotide sequences (D)

DETAILED DESCRIPTION

Figure 3:
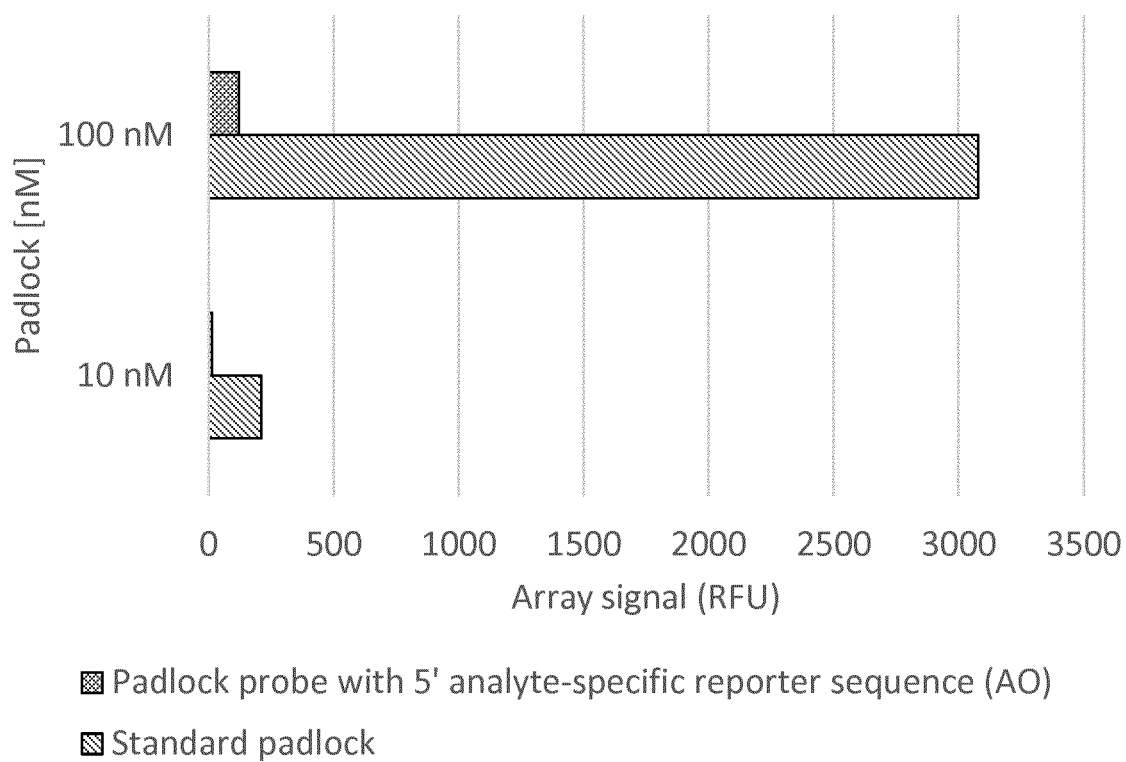
FIG. 3 shows signals generated by pools of padlock probes with and without 5' analyte-specific reporter sequences.

The present invention seeks to eliminate the source of background signal in RCA by re-designing padlock probes such that any non-target specific signal generated as a result of the non-specific binding described above is not detected, or more particularly is removed and thus is not detected. Specifically, this may be achieved by providing padlock probes which comprise a reporter sequence 5' to a cleavage site, and performing a cleavage reaction to remove the 5' reporter sequence from any non-circularized padlock probes. This may include any non-hybridized probes (unreacted padlock probes free in solution) and/or any non-specifically hybridized padlock probes. This has the benefits that the 5'-most reporter sequence in any extension product formed as a result of the non-specific binding of a padlock probe to an RCP are removed and thus not detected, as well as degrading any remaining non-circularized padlock probes present in the sample following an RCA, thereby preventing them from being circularized in a target-independent manner in a subsequent step. Thus, the background signal level in the reaction may be reduced.

FIG. 1 provides a schematic illustrating such a situation for padlock probes which comprise an array oligonucleotide sequence (A) which (or the complement of which) allows binding to a complementary oligonucleotide on an array, and a detection oligonucleotide sequence (D) which (or the complement of which) is capable of hybridizing to a detection oligonucleotide for detection of the amplification products of the padlock on the array. A and D can accordingly be viewed as reporter sequences for the padlock probes. A1 and D1 are the A and D sequences for a first padlock probe A1, to detect a first analyte A1 and A2 is the A sequence for a second padlock probe A2 to detect a second analyte A2. R is a restriction oligonucleotide sequence. FIG. 1A and FIG. 1B show the unwanted non-specific hybridization and extension of the second padlock A2 on the RCP generated from the first padlock A1. As can be seen in FIG. 1A where the A sequence is 3' of R, restriction cleavage of the unwanted non-specific extension products leads to the excision of a monomer, which can be detected, and which in this particular case can be circularized into a new template for RCA (circle A2), which leads to amplification of the "wrong" (i.e. A2) signal. In FIG. 1B, where the A sequence is 5' of R, cleavage of the wrong extension products removes the incorrect A2 sequence, which cannot subsequently be detected, or amplified. Indeed it can be seen that a benefit of this arrangement is that the unwanted extension product of the second padlock probe A2, leads to the generation of a concatemeric amplicon containing more monomers corresponding to the "correct" first padlock probe A1, which can be amplified and detected, and therefore amplifies the "correct" signal.

It will be appreciated, however, that whilst advantageous, a cleavage step is not strictly necessary, and rather than physically removing by cleavage any non-target specific signal generated as a result of the non-specific binding of a padlock probe, the probe may instead be designed such that no amplification of the non-specific signal occurs. This may be achieved by designing the probe with amplification primer binding sites positioned such that it is not possible for amplification of the reporter sequence of an unligated (i.e. non-circularized) padlock probe to occur. Thus, for example, in the context of a method in which an RCA reaction generates a RCP which is subsequently detected by a further amplification reaction (such a PCR or similar reaction, etc.), and the further amplification reaction requires at least two (i.e. at least first and second) amplification primers, the probe may be designed such that the binding site for the second primer (e.g. a reverse primer) is not present 5' of the reporter sequence. In this way, it will not be possible for the reporter sequence (as contained in the padlock probe) to be amplified as there is no binding site for an amplification primer flanking the reporter sequence in the sequence of the padlock probe on the 5' side.

Thus, where a non-specific extension product is formed by extension of a padlock probe which has hybridized non-specifically to a RCP, the sequence of the padlock probe will represent the 5'-most monomer unit of the concatemeric extension product (which is complementary to the concatemeric RCP which templated its formation). The reporter sequence as contained in the padlock probe thus represents the 5'-most reporter sequence of the extension product. Where the padlock probe lacks an amplification primer binding sequence 5' to the reporter sequence, this 5' most reporter sequence cannot be amplified, as there are not two amplification primer binding sites flanking the reporter sequence. However, in the extension product downstream of the padlock probe, due to its concatemeric nature, amplification primer binding sites for the first and second amplification primers will flank the reporter sequence. Thus first and second amplification primers may be designed to flank a reporter sequence in a RCP, but the padlock probe itself will not contain a binding site for a second amplification primer which is 5' of the reporter sequence. By analogy to FIG. 1B, it may be possible for a first amplification primer to hybridize to the probe sequence of an extension product of the "wrong" padlock probe and thereby to extend over the "wrong" reporter sequence, but the absence of a primer binding site 5' of the "wrong" reporter sequence in the probe means that the 5' most "wrong" reporter sequence which is contained in the padlock probe sequence cannot be amplified because there is no binding site for the second primer required for the amplification (e.g. the reverse primer). As for the situation in FIG. 1B, however, the remainder of the concatemeric extension product has the "correct" reporter sequence, and thus, beneficially, the correct reporter sequence can be amplified.

Accordingly, in a first aspect the present invention provides a multiplexed method of detecting an analyte in a sample using two or more padlock probes each specific to a different target sequence, the target sequence being either part of an analyte or indicative of the presence of an analyte in the sample, the method comprising:

(a) contacting the sample with the two or more padlock probes and allowing the probes to hybridize to their respective target sequences, if present;

(b) circularizing any padlock probe which has hybridized to its target nucleic acid sequence by ligation to form a rolling circle amplification (RCA) template;

(c) amplifying ligated padlock probes by performing at least a linear RCA reaction using the RCA template(s) formed in step (b) to form first rolling circle amplification product(s) (RCP), wherein a first RCP is a concatemer comprising monomers which are complementary to the circularized padlock probe which templated its formation, and optionally, simultaneously with or subsequently to the linear RCA reaction, performing a further amplification reaction to amplify the first RCP(s);

(d) optionally, performing, during or after step (c), a restriction cleavage step; and (e) detecting the amplification product(s) to detect the analyte(s);

wherein each padlock probe comprises (i) 5' and 3' end sequences capable of hybridizing to a different target nucleic acid sequence, such that upon the hybridization the ends of the padlock probe are brought into juxtaposition, directly or indirectly, for ligation to circularise the padlock probe; and between the 5' and 3' end sequences:

(ii) at least one reporter sequence, at least one of which reporter sequences is an analyte-specific reporter sequence; and (iii) a restriction oligonucleotide (RO) sequence capable of hybridizing to a complementary sequence to create a restriction cleavage site, wherein the RO sequence is located 3' of the analyte-specific reporter sequence, and/or a first amplification primer binding site for a further amplification reaction;

and wherein where the padlock probe comprises an RO sequence, the restriction cleavage of step (d) uses a restriction enzyme capable of cleaving the restriction cleavage site, optionally together with a restriction oligonucleotide which is complementary to and capable of hybridizing to the restriction oligonucleotide (RO) sequence, and cleavage at the restriction cleavage site occurs 3' of the analyte-specific reporter sequence, and where the padlock probe comprises a first amplification primer binding site for the further amplification reaction, it does not contain a second amplification primer binding site 5' of the analyte-specific reporter sequence.

As noted above, where the padlock probe comprises a binding site for the first amplification primer of a further amplification reaction, and particularly where the probe does not comprise a RO sequence, the critical requirement is that the padlock probe does not contain a second amplification primer binding site 5' of the analyte-specific reporter sequence. The position of the first amplification primer binding site is not critical or limited, and it may accordingly be present 5' of, 3' of, or within the analyte-specific reporter sequence, e.g. 3' of or within the analyte-specific reporter sequence. In this context it will be understood that the term "amplification primer binding site" (or binding site for an amplification primer, or such like) is to be interpreted to include both polarities. Thus, an amplification primer may bind to the primer binding site as present in the padlock probe or to a sequence complementary to the primer binding site, as present in a complementary copy of the padlock probe.

Although with such a design for the amplification primers, a cleavage step is not necessary, a cleavage step is advantageous, particularly where the cleavage step results in cleavage of the first RCP into monomers. Thus, where a further amplification reaction of a first RCP is carried out, it is advantageous to cleave the RCP and/or its amplicons into monomers before, during or after performing the subsequent amplification reaction, as this generally results in less background and a "cleaner" reaction. Accordingly, preferred embodiments of the method include a RO sequence in the probe design and comprise a cleavage step.

Thus, in a more particular further aspect the present invention provides a multiplexed method of detecting an analyte in a sample using two or more padlock probes, wherein each padlock probe comprises 5' and 3' end sequences capable of hybridizing to a different target nucleic acid sequence, which target sequence is either part of an analyte or is indicative of the presence of the analyte in the sample, such that upon the hybridization the ends of the padlock probe are brought into juxtaposition, directly or indirectly, for ligation to circularise the padlock probe, and wherein each padlock probe comprises, between its 5' and 3' ends, a restriction oligonucleotide (RO) sequence capable of hybridizing to a complementary sequence to create a restriction cleavage site, and at least one reporter sequence, at least one of which is an analyte-specific reporter sequence, and the RO sequence is located 3' of the analyte-specific sequence such that cleavage at the restriction cleavage site can occur 3' of the analyte-specific reporter sequence, the method comprising:

(a) contacting the sample with the two or more padlock probes and allowing the probes to hybridize to their respective target sequences, if present;

(b) circularizing any padlock probe which has hybridized to its target nucleic acid sequence by ligation to form a rolling circle amplification (RCA) template (specifically a first RCA template);

(c) performing a RCA reaction which comprises at least a linear RCA reaction using the RCA template(s) formed in step (b) to form first rolling circle amplification product(s) (RCP), wherein a first RCP is a concatemer comprising monomers which are complementary to the circularized padlock probe which templated its formation;

(d) during or after step (c), performing a restriction cleavage step using a restriction enzyme capable of cleaving the restriction cleavage site, optionally together with a restriction oligonucleotide which is complementary to and capable of hybridizing to the restriction oligonucleotide (RO) sequence; and (e) after step (d), detecting the amplification product(s) to detect the analyte(s).

The amplification products which are detected (e.g. detected in step (e) of the method above) may be RCA amplification products (that is RCPs). However, in other embodiments, discussed in more detail below, the amplification products detected may be the products of a further amplification reaction which is not a RCA (or RCA-based) amplification reaction (i.e. the further amplification reaction may be a non-RCA amplification reaction).

As described in more detail below, the method may comprise an amplification of the first RCP (i.e. the concatemer directly generated through the linear RCA reaction using the circularized padlock probe as RCA template). Such an amplification may take place as part of the RCA reaction of step (c), for example when this is a HRCA reaction, or it may be a further or separate amplification reaction, e.g., a C2CA reaction, or a PCR or similar reaction. Accordingly RCA or other amplification products include not only the product resulting from the linear first RCA reaction, but also any amplicons thereof. As described further below, they may also comprise the cleavage products of any RCA or other amplification products. Further, the amplification products may have the same or the opposite polarity to the padlock probe from which they were generated. Thus, they may comprise a sequence (or more particularly multiple copies thereof) which is the same as (or homologous to) the padlock probe, or they may comprise a sequence (or more particularly multiple copies thereof) which is complementary to the padlock probe. Amplification products of the same and/or opposite polarity may be detected. This may depend upon the choice of manner in which the products are detected.

The method of the present invention is a multiplexed method of detecting an analyte in a sample. In this context, the term "multiplexed" refers simply to the use of two or more different padlock probes together in the same method. It is accordingly not required that all the steps of the method are carried out in the same reaction vessel, or in the same reaction, or reaction mixture. In a particularly preferred embodiment the two or more padlock probes are used in the same reaction, in the sense of being present or added to the same reaction mixture or reaction vessel. In other words in such a multiplexed method the two or more padlock probes are added to the same sample, (which includes the same part (i.e. the same portion, fraction or aliquot etc.) of the sample). Subsequent steps of the method may be performed in the same reaction mixture, or reaction vessel etc. In other embodiments, however, some or all of the steps may be performed in separate reaction mixtures or vessels etc. Thus, it is included that the method of the invention, or that one or more steps of the method, may be performed in parallel. That is, separate reactions may be performed with separate padlock probes in parallel reactions (e.g. the initial sample may be divided into aliquots for separate reactions), or the padlock probe reaction steps may be performed together, and subsequent steps may be performed separately in parallel, etc. In particular, the steps up to amplifying circularized padlock probes to form at least first RCPs may be performed together, and steps of detecting the amplified products may be conducted in parallel (i.e. the amplified reaction mixture may be divided into aliquots for subsequent detection steps).

For example, in one typical format the padlock probes may be added to the sample, hybridized, ligated, and subjected to an RCA reaction (to produce a least a first RCP), before the procedure is continued in parallel. Further, the amplicons (e.g. the first RCP, and optionally other, subsequent, amplicons (if present)) may be subjected to cleavage into monomers before the procedure is continued in parallel. Thus, in such embodiments the reaction mixture may be divided into aliquots after step (c), or after cleavage step (d), where such a cleavage step is included in the method. Thus the detection step (e) may be carried out on separate aliquots of the reaction mixture, e.g. on separate aliquots of the amplification products. As described in more detail below, the detection step (step (e)) may involve an amplification reaction. Alternatively expressed, a further amplification reaction may be performed before step (e), after the reaction mixture (comprising e.g. the first RCP or cleaved monomers thereof) has been divided into aliquots. Thus, a further amplification reaction may be performed on separate aliquots in parallel after step (c) or after step (d), but before step (e). Such a further amplification reaction may in some embodiments include a RCA reaction and in other embodiments the further amplification reaction may be a non-RCA amplification reaction, e.g. a PCR or other amplification reaction using at least two amplification primers. As described below, in other embodiments, a further amplification reaction may take place during step (c), and in such embodiments, the amplified (and optionally cleaved) amplification products may be aliquoted for subsequent detection in parallel.

Thus, although a multiplexed assay method of the invention may involve assaying for two or more analytes, and hence two or more padlock probes specific for different analytes may be used, as described in more detail below, the method of the invention encompasses the use of two or more padlock probes which may detect the same analyte (i.e. which are specific for the same analyte) but which are designed to hybridize to different target sequences to detect that analyte. In such a case the two or more padlock probes will each detect the same analyte but are different to one another (at least in having 3' and 5' end sequences which are specific for different target sequences, and in some embodiments in further having different reporter sequences, although this is not a requirement). In practice the two or more padlock probes may comprise two or more padlock probes each specific for a different analyte, and two or more different padlock probes, each specific for the same analyte.

The principles of using padlock probes to detect target nucleic acid sequences are well-known in the art, and are described for example in WO 95/22623. In summary, sequences at the 5' and 3' ends of a padlock probe are complementary to and capable of hybridizing to adjacent or nearby sequences in a target nucleic acid sequence, such that the hybridization of the padlock probe to the target nucleic acid sequence results in the ends of the probe being brought into juxtaposition for direct or indirect ligation, which results in circularization of the padlock probes.

The target nucleic acid sequences which are the targets for binding by the padlock probes may be part of an analyte (i.e. the analyte itself may be bound directly by a padlock probe and thereby template the circularization of the padlock probe), or may be indicative of the presence of the analyte in the sample. As such, a target nucleic acid sequence may be viewed as a marker, or proxy, for the analyte; the analyte need not itself be or comprise the target nucleic acid sequence. For instance, the target nucleic acid sequence may be attached to the analyte, e.g. it may be a nucleic acid domain of an antibody:nucleic acid conjugate which is bound, directly or indirectly, to the analyte. Similarly, the target nucleic acid sequence to be detected may be a nucleic acid molecule generated from the interaction between proximity probes, which are bound to the target analyte, e.g. a protein. In this way, an analyte may be 'represented' by a target nucleic acid sequence, or put another way, a given target nucleic acid sequence may be seen to be 'representative of' an analyte in the sample.

Each of the padlock probes that are used in the methods of the present invention is capable of hybridizing to a different target nucleic acid sequence. In other words, each of the padlock probes has different sequences at its 5' and 3' ends which direct it to hybridize (bind) to a different target nucleic acid sequence present in the sample (thus to indicate the presence thereof). The use of two or more padlock probes in the multiplexed detection method of the present invention accordingly allows the detection of two or more different target nucleic acid sequences in a sample. As each target nucleic acid sequence is representative of an analyte, each padlock probe may thereby be considered to be 'for' detecting that analyte, i.e. the analyte for which the target nucleic acid sequence is representative. In other words, each padlock probe is a padlock probe for a particular analyte, and is targeted to that analyte by its respective target nucleic acid sequence.

It is noted, however, that it is not required that every padlock probe used in the methods of the present invention will hybridize to its respective target nucleic acid molecule, and only one or a selection of padlock probes may hybridize to their respective target nucleic acid molecules, depending on the target nucleic acid molecules that are present in the sample (which in turn will depend on the nature of the analyte or analytes present in the sample). Thus it is possible that fewer target nucleic acid molecules may be present in the sample than padlock probes that are added to the sample, and only those padlock probes for which there are target nucleic acid molecules will be circularized, and thus indicate the presence of their respective analytes in the sample. In this sense multiple padlock probes each specific for a different analyte may be used (or included in the probes that are used), but only one or a subset of the analytes assayed for may actually be detected as a result of the method.

The specificity of the methods of the present invention is directed by the target nucleic acid sequence and the analyte-specific reporter sequence of each padlock probe. Each padlock probe is specific for a different target nucleic acid sequence, and the detection of that target sequence will involve the generation and detection of an amplification product (i.e. a RCA product; RCP) which comprises a given analyte-specific reporter sequence or its complement (depending on the nature of the RCA reaction of step (c) and on whether there is any amplification of the first RCP), and the detection of the analyte-specific reporter sequence may indicate the presence of a particular analyte in the sample. The target specific nucleic acid sequence is representative of a particular analyte, and thus the presence of a particular target nucleic acid sequence in the sample also indicates the presence of that particular analyte in the sample.

Thus, as each padlock probe is specific to a different target nucleic acid molecule, the analyte-specific reporter sequence of each of the padlock probes can be thought of as being specific to a particular analyte, i.e. it may be used to indicate the presence of that analyte in the sample. However, whilst each padlock probe comprises 5' and 3' end sequences capable of hybridizing to a different target nucleic acid molecule, the analyte-specific reporter sequences of each padlock are not limited to being different, as described in greater detail below, and in certain embodiments of the present invention two or more of the padlock probes may comprise the same analyte-specific reporter sequence (and thus will indicate the presence of the same analyte), despite being capable of hybridizing to different target nucleic acid sequences. In such an embodiment, a single analyte may be detected by more than one padlock probe.

Padlock probes which are specific for the same analyte may be detected separately (individually) and/or collectively (i.e. as a group) depending upon the reporter sequences which they contain. Thus, padlock probes specific for the same analyte may in one embodiment contain the same analyte-specific reporter sequence and in another embodiment they may contain different analyte specific reporter sequences. Accordingly, two or more padlock probes which have the same analyte-specific reporter sequence can allow two or more different target nucleic acid sequences to represent the same analyte. An analyte specific reporter sequence may accordingly be a unique reporter sequence in each of the two or more padlock probes which are used, but in many embodiments it will not be. Padlock probes which have the same analyte-specific reporter sequence may further contain a separate target-specific reporter sequence, but this is not a requirement. One of more of the reporter sequences in a padlock probe (or their complements) may be detected in step (e) to detect the amplification products. In certain preferred embodiments the analyte-specific reporter sequence is a capture sequence for capturing the resulting RCA amplification product of that probe on a solid surface such as an array, e.g. an array oligonucleotide sequence as mentioned above and discussed further below. However, in other embodiments a target-specific reporter sequence may be a capture sequence, and optionally the padlock probe may comprise a further analyte-specific reporter sequence for detection of captured (e.g. immobilized) amplification products. In still further embodiments, the analyte-specific reporter sequence, may be, or may comprise an amplification primer binding site. Hence, analyte-specific amplification primers may be used to detect the analyte. Thus, in one embodiment of the present invention, the analyte-specific reporter sequence of each padlock probe is different, and the detection of an amplification product by means of that reporter (i.e. detecting that reporter sequence or its complement in an amplification product) will indicate the presence of a particular target nucleic acid sequence, and thus of a particular analyte, in the sample. Accordingly, in certain embodiments, the analyte-specific reporter sequence of each padlock probe may be specific for a different analyte.

However, in other embodiments of the present invention, the analyte-specific reporter sequence of two or more of the padlock probes may be the same, and thus the detection of a RCP arising from either one of the padlock probes will indicate the presence of a particular analyte in the sample. In this way, two or more different padlock probes may be used to indicate the presence of the same analyte (although as defined above, this takes place via hybridization to a different target nucleic acid sequence).

In certain embodiments, each analyte in the sample may be represented by a single different target nucleic acid sequence. Thus, in embodiments discussed above in which each padlock probe comprises a different analyte-specific reporter sequence, the detection of each different analyte by hybridizing a padlock probe to a different target nucleic acid sequence results in the generation of a different RCP comprising a different analyte-specific reporter sequence or complement thereof.

In other embodiments, a single analyte may be represented by two or more different target nucleic acid sequences, such that detection of any one or more of the target nucleic acid sequences that are representative of that analyte will indicate the presence of that analyte in the sample. In such embodiments, each of the padlock probes may comprise a different analyte-specific reporter sequence, such that detection of any of the RCPs (each comprising a different analyte-specific reporter sequence or complement thereof) that are formed in the methods of the present invention will indicate the presence of an analyte in the sample. However, advantageously, two or more padlock probes which are capable of hybridizing to different target nucleic acid molecules representative of the same analyte may comprise the same analyte-specific reporter sequence, such that each of the RCPs formed in the methods of the present invention will comprise the same analyte-specific reporter sequence or complement thereof.

The "analyte" is the ultimate target of the assay, that is it is the target, or objective, of the detection method of the invention, or the "subject" or substance or material (i.e. the entity/entities) it is desired to detect. It is accordingly defined on the basis of the desired "read-out" of the detection method. It may be a single species, in the sense of a single entity (e.g. a single taxonomic species or strain of organism, e.g. microorganism) or it may be a group of entities, which may be related entities, i.e. a broader group or set comprising a number of different single species (e.g. a taxonomic genus, or wider group of organisms, or compounds or other entities etc.). Thus, an analyte can be defined with specific particularity (e.g. a single species or strain of organism, or a single compound or isoform), or with variable (i.e. lesser or greater) degrees of generality (e.g. a genus of organism, or a class or type of organism (e.g. gram positive bacteria, yeast, a class of protein molecule etc.). Put another way, the analyte may be a 'generic' analyte, and may include more than one specific entity.

Accordingly, padlock probes capable of hybridizing to different target nucleic acid molecules representative of different entities which may be the analyte (i.e. different members of the group which makes up the analyte) may comprise the same analyte-specific reporter sequence. In such embodiments, the amplification products resulting from any of the padlock probes will comprise the same analyte-specific reporter sequence or complement thereof.

Detection of the RCPs will therefore indicate the presence of any one of the generic analyte (i.e. the analyte group) which is present in the sample. In other words, the presence of any one of a generic analyte group in the sample may be indicated by the same analyte-specific sequence, or alternatively put, the presence of one of a generic analyte group may be indicated by the formation of an RCP comprising the same analyte-specific reporter sequence, or complement thereof. Accordingly, detection of an amplification product arising from any one member of a generic analyte group may indicate that that the analyte is present in the sample.

Thus, the target specific nucleic acid sequences provide information on whether a particular analyte is present in the sample, whereas the analyte-specific reporter sequences dictate the level of specificity with which an analyte may be detected. As each padlock probe is capable of hybridizing to a different target nucleic acid sequence, the level of specificity of the method of the present invention (i.e. the specificity with which an analyte may be distinguished from another analyte in the sample) depends on whether and which padlock probes share the same analyte-specific reporter sequence.

The analyte-specific reporter sequence is specific for the analyte that is to be detected, and the level of specificity or generality with which a given analyte is to be detected may depend on whether the analyte-specific reporter sequence is unique to a single probe or is provided in two or more different padlock probes.

By way of representative example, the method of the present invention may be used to detect a microorganism present in a sample. Thus, padlock probes capable of hybridizing to target nucleic acid sequences which may be representative of different types of microorganisms are used. However, depending on the level of specificity that is required from the microbial detection, the padlock probes may be designed such that the analyte-specific reporter sequences of two or more of the padlock probes are specific for the same analyte, e.g. to a strain, sub-species, species, genus, family, order, class, phylum or kingdom of a microorganism in a sample, or to Gram positive or Gram negative bacteria. For example, if it is only required to detect whether a microorganism in a sample is Gram-positive, padlock probes capable of hybridizing to different target nucleic acid sequences which are representative of various different Gram positive bacteria may be used. However, each of these padlock probes may comprise a common analyte-specific reporter sequence, and thus the detection of an RCP comprising this analyte-specific reporter sequence (or its complement) would indicate the presence of a Gram positive bacterium in a sample. By contrast, however, if the analyte of the assay is a specific strain of *E. coli*, a padlock probe or padlock probes capable of hybridizing to a target nucleic acid sequence or target nucleic acid sequences which are representative of that specific strain may be used. If two or more target nucleic acid sequences are provided for that strain, each padlock probe may similarly comprise a common analyte-specific reporter sequence, whereby detection an RCP arising from any one of those padlock probes would indicate the presence of that specific *E. coli* strain.

Where the analyte is not, or does not comprise, a nucleic acid molecule, the sample may be contacted with one or more reagents to provide, or to generate, the target nucleic acid sequence for the analytes in the sample. The methods of the present invention may therefore comprise a step of binding a molecule comprising a target nucleic acid sequence to an analyte, and/or generating a molecule comprising a target nucleic acid sequence, prior to performing steps (a)-(e) of the present invention. Thus the target nucleic acid sequence may be, or may be comprised in, a target nucleic acid molecule. Methods for this are well known in the art, and may comprise contacting the sample with one or more binding agents, capable of binding specifically to a target analyte, wherein the binding agents are provided with a target nucleic acid molecule, or are capable of generating a target nucleic acid molecule. The binding agent may for example be an antibody or antibody fragment or derivative, or any other affinity binding molecule. For example, a target nucleic acid molecule may be generated from the interaction of two or more proximity probes when they have bound simultaneously to the target analyte. Proximity probes are well known and described in the literature and in particular embodiments comprise an analyte-binding domain coupled to a nucleic acid domain. When the probes have bound in proximity to their target analyte, the nucleic acid domains may interact, leading to the generation of a detectable signal, in this case a target nucleic acid sequence which may be detected by the methods of the present invention. For example the nucleic acid domains may be ligated together to form a "new" target nucleic acid molecule, or they may template and/or prime the generation of an extension product which provides the target nucleic acid sequence, or they may template the ligation of one or more added oligonucleotides, which generates or leads to the generation of a target nucleic acid molecule. For example the target nucleic acid molecule may be the amplicon of a nucleic acid molecule arising from the interaction of nucleic acid domains of proximity probes.

The analyte may accordingly be any entity, e.g. any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead to the generation of a target nucleic acid sequence.

Analytes of particular interest may thus include nucleic acid molecules, such as DNA (e.g. genomic DNA, mitochondrial DNA, plastid DNA, viral DNA etc.) and RNA (e.g. mRNA, microRNA, rRNA, snRNA, viral RNA etc.), and synthetic and/or modified nucleic acid molecules, (e.g. including nucleic acid domains comprising or consisting of synthetic or modified nucleotides such as LNA, PNA, morpholino etc.), proteinaceous molecules such as peptides, polypeptides, proteins or prions or any molecule which includes a protein or polypeptide component, etc., or fragments thereof. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

Identification of RNA may be accomplished via cDNA, for instance by using a suitable reverse transcriptase (RT) primer. A RT primer may be used, binding to the target RNA at a site which is upstream of a recognition site for a padlock probe, (more particularly upstream of the complement of the recognition site in the cDNA). Extension of the primer produces a cDNA molecule comprising the target nucleic acid sequence for a padlock probe, and the padlock probe may thereby be used to report the presence and identity of the cDNA, and therefore of the RNA molecule. It may thus be possible to avoid the requirement to replicate an entire RNA molecule in order to identify it; it is only necessary to extend the primer to cover the probe recognition site. Thus the time required for the initial extension step may be reduced. Extension may be performed for 10, 20, 30, 40, or 50 seconds, or 1, 2, 3, 4, 5, or 10 minutes to reduce the length of time required to identify an RNA molecule in a sample.

The sample may be any sample which contains an analyte, and includes both natural and synthetic samples, that is materials which occur naturally or preparations which have been made. Naturally occurring samples may be treated or processed before being subjected to the methods of the invention. All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue green algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc.), tissues, biopsies, cell cultures, cell suspensions, conditioned media or other samples of cell culture constituents, etc. The sample may be pre-treated in any convenient or desired way to prepare for use in the methods and uses of the invention, for example by cell lysis or purification, isolation of the analyte, etc.

In one particular embodiment the sample comprises microbial cells which have been isolated from a clinical sample or from a culture of a clinical sample. In such a sample the target nucleic acid sequence of a padlock probe may be a nucleotide sequence present in a microbial cell, e.g. a nucleotide sequence which is characteristic for, or discriminatory or identificatory of a microbial cell, at any level, e.g. at type, group, class, genus, species or strain level.

The restriction cleavage step (step (d)) results in cleavage of nucleic acid molecules present in the sample (or alternatively expressed, present in the reaction mixture formed in or arising from the preceding method steps, starting from addition of the padlock probes to the sample) which have formed a restriction cleavage site comprising the restriction oligonucleotide (RO) sequence of a padlock probe (e.g. by hybridization of a complementary sequence to a restriction oligonucleotide (RO) sequence in an unligated padlock probe or an amplicon thereof, or to a complement thereof, e.g. in an unwanted extension product). Any sequence 5' to the restriction cleavage site is thereby separated from the 3' end of any such molecule. In other words, the sequence 5' to the restriction cleavage site is removed.

In this way if any extension product is formed by an oligonucleotide or other nucleic acid molecule (e.g. an unligated padlock probe) binding to the first RCP and acting as a primer for an extension reaction using the first RCP as an extension template prior to the cleavage step, any sequence 5' to the 5'-most restriction cleavage site within any such extension product will be removed during cleavage step (d). Any extension product formed in this way will comprise a concatemeric repeat of the complementary sequence of the monomers of the first RCP (i.e. it will comprise multiple tandem repeats of the sequence of the RCA template used to generate the first RCP), and a sequence at its 5' end, 5' to a restriction cleavage site. The extension product will therefore comprise multiple copies of the analyte-specific reporter sequence of the padlock probe used to generate the RCA template, and a further sequence deriving from any oligonucleotide binding to the first RCP and acting as a primer for an extension reaction. Such unwanted extension products generated using the first RCP as a template may themselves serve as templates for extension and so may be propagated, or amplified (in other words, an unwanted, non-specific HRCA reaction may occur). Such unwanted extension products may form double-stranded constructs which contain restriction cleavage sites comprising the RO sequence and hence also will be cleaved.

Thus, if an unligated padlock probe binds to the first RCP and acts as a primer for an extension reaction, the resulting extension product will comprise a concatemeric repeat of the complementary sequence of monomers of the first RCP, and thus will comprise multiple copies of the analyte-specific reporter sequence of the padlock probe used to generate the RCA template for the RCA reaction. The extension product will, however, further comprise at its 5' end the analyte-specific reporter sequence of the bound unligated padlock probe. In one embodiment, the object of the present invention is to enable this sequence to be removed from the extension product as a result of step (d). Thus, the restriction cleavage step may remove the analyte-specific reporter sequence provided by any non-specifically bound padlock probes. In this way, the analyte-specific reporter sequence introduced into the extension product by the non-specific binding of an unligated padlock probe may be removed (and thus not detected), whilst the remainder of the extension product itself beneficially increases the number of copies of the analyte-specific reporter sequence present in the sample, and can increase the efficiency with which the analyte is detected in the sample. Thus, a previously undesirable non-specific interaction, which would otherwise deleteriously affect the readout of a multiplexed detection assay, may be harnessed to improve the efficiency with which an analyte is detected in the sample by the method of the present invention.

The restriction cleavage step requires the formation of a double-stranded nucleic acid molecule, in order for a restriction cleavage site to be formed. In other words, restriction oligonucleotide sequences must hybridize to a complementary nucleic acid sequence in order for a restriction cleavage site to be formed, and thus in order for cleavage to take place. The formation of the restriction cleavage site in this way may be by the hybridization to the first RCP of a molecule present or generated (e.g. by an unwanted extension reaction) in the sample/reaction mixture which contains a sequence complementary to the restriction oligonucleotide (RO) sequence, or may be by the addition of a separate restriction oligonucleotide. Thus, optionally, a restriction oligonucleotide is used to perform restriction cleavage step (d).

In some embodiments, an oligonucleotide (e.g. an unligated padlock probe) may hybridize to the first RCP in such a way that a restriction cleavage site is formed between the oligonucleotide and the first RCP. In such a case, cleavage may take place without the addition of any restriction oligonucleotide, as the restriction cleavage site may be formed directly through the binding of the oligonucleotide to a complementary sequence the first RCP. In this way, an unligated padlock probes which binds to the first RCP may be cleaved using a restriction enzyme.

In other embodiments, the hybridization of an oligonucleotide to the first RCP may not directly result in the formation of a double-stranded restriction cleavage site, e.g. if the oligonucleotide does not comprise a restriction oligonucleotide (RO) sequence. A restriction cleavage site may, however, be formed by extension of the oligonucleotide; as the first RCP comprises a concatemer of monomers complementary to the circularized padlock probe, the double-stranded nucleic acid molecule formed following extension will comprise a restriction oligonucleotide (RO) sequence in one strand, which sequence will be hybridized to a complementary sequence in the opposite strand. Thus, a restriction cleavage site may be formed between the first RCP and an extension product. Analogously, subsequent generations of extension products, which may be generated in an unwanted non-specific HRCA reaction, may contain restriction sites comprising the RO sequence and its complement.

Similarly, if the oligonucleotide which hybridizes to the first RCP comprises a restriction oligonucleotide (RO) sequence (e.g. it is an unligated padlock probe), and this sequence is not hybridized to a complementary sequence in the first RCP, hybridization of a further oligonucleotide to a portion of the hybridized oligonucleotide (or any extension product formed therefrom) and extension of that further oligonucleotide will result in the formation of a double-stranded nucleic acid molecule which comprises a restriction oligonucleotide (RO) sequence in one strand, and a complementary sequence in the opposite strand, thereby forming a restriction cleavage site. Thus, if the oligonucleotide which binds to the first RCP comprises a restriction oligonucleotide sequence towards its 5' end (e.g. if it is an unligated padlock probe), binding of a further oligonucleotide 3' to this restriction oligonucleotide sequence (either directly to the hybridized oligonucleotide or to an extension product), and extension of that further oligonucleotide from its 3' end will result in the formation of a restriction cleavage site. Cleavage step (d) will therefore remove any part of the hybridized oligonucleotide 5' to this restriction site as described above.

In yet other embodiments where an oligonucleotide comprising a restriction oligonucleotide (RO) sequence (e.g. an unligated padlock probe) hybridizes to the first RCP and does not result in the formation of a restriction cleavage site as described above, a restriction oligonucleotide may be used in the restriction cleavage step (restriction cleavage step (d)) to create the restriction site for cleavage. The restriction oligonucleotide may bind to a restriction oligonucleotide (RO) sequence present in an oligonucleotide in the sample, including both oligonucleotides which have bound to the first RCP, and any oligonucleotides which have not bound to the first RCP which comprise a restriction oligonucleotide (RO) sequence. In this way, a restriction cleavage site may be created in unligated padlock probes, both which have and have not bound to the first RCP. Thus, the addition of restriction oligonucleotides may beneficially be used in restriction step (d) to remove the analyte-specific reporter sequence from unligated padlock probes.

A restriction oligonucleotide may be added during or after any of the steps preceding step (d), including during step (d) itself.

The restriction cleavage step performed in step (d) therefore may act to cleave any padlock probes which have not been circularized, i.e. any unligated padlock probes. As the analyte-specific reporter sequence is provided 5' to the restriction cleavage site in the padlock probes, the analyte-specific reporter sequence is separated from the 3' end of the padlock probes following the restriction cleavage step. In other words, the analyte-specific reporter sequence is removed from any unligated padlock probes.

More particularly, in step (d) any unligated padlock probes which have hybridized non-specifically to the first RCP are cleaved to remove the analyte-specific reporter sequence (more particularly an incorrect, or non-specific, or off-target analyte reporter sequence). As will be clear from the above, the formation of a cleavage site does not require a restriction oligonucleotide to be added, if a double-stranded restriction site is formed by hybridization, or hybridization and extension. More advantageously, in step (d) any subsequent generations of unwanted extension or amplification products generated from a non-specifically hybridized and extended padlock probe are cleaved. The extent of background from such unwanted extension/amplification reactions will depend upon the polarity of the amplification product which is detected—if in step (e) only amplification products which comprise the complement of the padlock probe are detected (i.e. opposite polarity to the ("correct") padlock probe), then the first extension product which is the result of extension of the non-specifically hybridized padlock probe will not be detected. However, if step (e) includes detecting amplification products which have the same polarity as the padlock probe (i.e. comprise a sequence which is the same as or homologous to the padlock probe), the first extension product which is the result of extension of the non-specifically hybridized padlock probe may be detected.

In certain embodiments, restriction cleavage step (d) may result in the cleavage of the first RCP, and/or of any subsequent amplification products, e.g. products of a C2CA reaction, into monomers, either with or without the use of restriction oligonucleotides in combination with the restriction enzyme in step (d). The monomers generated in this cleavage step may be detected in step (e), i.e. cleaved monomers (including cleaved monomers arising from any subsequent amplification step) may be detected in step (e) to detect the analyte. The term "cleaved monomer" thus means a monomer which results from cleavage of a concatemeric RCA product (RCP), which may be the first RCP or a subsequent generation of RCP. More particularly, the cleaved monomer is released by cleavage of a concatemeric RCP at a restriction site comprising the RO sequence.

Cleavage of the desired ("correct") RCA product also results in cleavage of non-specific extension and/or amplification products into monomers, and an additional sequence (a partial monomer) 5' to the 5'-most restriction cleavage site in the extension product. Each monomer thus formed therefore has the sequence of the first RCA template (or its complement), and thus comprises an analyte-specific reporter sequence (or its complement). However, the sequence 5' to the 5'-most restriction cleavage site is only a partial monomer, and comprises the analyte-specific reporter sequence of the unligated padlock probe which had bound to the RCA product. Advantageously, this sequence is not detected in step (e).

In embodiments of the present invention where an extension product is formed using the first RCP as an extension template, restriction cleavage sites may be formed by the interaction between the first RCP and the extension product (i.e. a double-stranded nucleic acid molecule is formed, comprising a restriction oligonucleotide (RO) sequence in one strand, and a complementary sequence in the opposite strand). Cleavage of the first RCP into monomers may also result in cleavage of any extension products formed using the first RCP as a template for extension, e.g. extension products formed by the non-specific binding of an oligonucleotide (such as an unligated padlock probe) to the first RCP.

However, in other embodiments in which no extension product is formed, the restriction cleavage site may be formed by a restriction oligonucleotide hybridizing to the sequence in the first RCP complementary to the restriction oligonucleotide (RO) sequence and forming a restriction cleavage site.

Thus, in certain embodiments, a restriction oligonucleotide may be used to create the restriction cleavage site in a desired concatemeric RCP. The restriction oligonucleotide may hybridize to the RCP at the sequence which is complementary to the restriction oligonucleotide (RO) sequence of the padlock probe, thereby to create a cleavage site in each monomer, and wherein the cleavage of step (d) results in cleavage of the concatemeric RCP into monomers. Thus, in the restriction cleavage step (d) the restriction site for cleavage may be created by hybridization of a restriction oligonucleotide to the RO sequence. The restriction oligonucleotide may be added during or after any step preceding the cleavage step (d), including during cleavage step (d) (i.e. it may be added during or after any of steps (a), (b) or (c).

Put another way, in certain embodiments of the present invention, the restriction oligonucleotide may hybridize to the first RCP at the sequence which is complementary to the restriction oligonucleotide (RO) sequence of the padlock probe, thereby to create a cleavage site in each monomer (of the concatemeric RCP), and wherein cleavage of step (d) results in cleavage of the concatemeric RCP into monomers. In such an embodiment, where a restriction oligonucleotide is used to generate desired cleavage sites in a first or subsequent RCP, cleavage sites may also be created in unwanted double-stranded non-specific extension and/or amplification products.

The restriction oligonucleotide (RO) sequence in each padlock probe may be different, i.e. a different restriction oligonucleotide may hybridize to the RCP formed from each padlock probe at a sequence that is complementary to the restriction oligonucleotide (RO) sequence of the padlock probe used to generate the RCP. However, in an alternative and preferred embodiment, the restriction oligonucleotide (RO) sequence in each of the padlock probes may be the same, and thus the same restriction oligonucleotide may be used to cleave the RCPs formed from each of the padlock probes as described above. Thus, in certain embodiments, the restriction oligonucleotide (RO) sequence may be a common RO sequence which is the same in all of the padlock probes.

Many restriction cleavage sites that are recognised by and cleaved by restriction enzymes comprise palindromic nucleotide sequences. A palindromic nucleotide sequence has the same sequence as its reverse complement, when read in the 5' to 3' direction (e.g. GGATCC is a palindromic nucleic acid sequence). Thus, in preferred embodiments, the restriction oligonucleotide (RO) sequence and the restriction oligonucleotide may be palindromic. In this way, the same restriction oligonucleotide may bind to both the RO sequence of the padlock probes, as well as its complement (e.g. the complement of the RO sequence in an RCP).

Following the linear RCA reaction, the first RCP may be further amplified prior to detection. Thus, in certain embodiments, the method of the present invention comprises further amplifying the product of the linear RCA during or after step (c) or (d), but before step (e) to increase the number of monomers present in the sample. Any desired means of amplification known in the art may be used.

In one preferred embodiment, amplification may comprise the circle-to-circle amplification (C2CA) method. C2CA was developed to allow greater than linear amplification in RCA. As described above, in this method, the first RCP (generated from a first "circle" or circular RCA template i.e. the circularized padlock probe) is cleaved into monomers as described herein. Following cleavage of the first RCP, the resulting monomers may be ligated into further circles which can be used as template for a second RCA, to form second RCPs. This process may be repeated one or more times (i.e. forming third, fourth fifth etc. RCPs, in third, fourth or fifth etc. RCA reactions), to further increase the number of monomers present in the sample.

Preferably, and in order to further reduce the contribution of background signal arising either from padlock probes themselves, or amplification products formed therefrom, the detection method is performed to detect the complement of the analyte-specific reporter sequence. Thus, where C2CA is performed, preferably, an odd number of RCA reactions are performed when increasing the number of monomers present in the sample, in order that the complement of the analyte-specific reporter sequence (rather than the analyte-specific reporter sequence itself) may be detected (as the complement of the complement of the first RCA product comprises the complement of the analyte-specific reporter sequence of the padlock probe).

Thus, in one particularly preferred embodiment, amplification comprises one or more rounds of a circle-to-circle amplification (C2CA) reaction, wherein the first RCP is monomerised and the monomers are ligated into further (secondary) circles which are used as RCA templates in a further (second) RCA reaction to generate a second RCP, which may optionally be monomerised, and optionally further subjected to a further round of C2CA to generate a third or further RCP, and optionally third or further generations of monomers.

In certain embodiments of the C2CA method, and as described in EP 2236622, circularization of the monomers formed following cleavage of the first RCP can be templated by a restriction oligonucleotide. That is, the same restriction oligonucleotide which is used to generate the restriction cleavage site for cleavage of a RCP is used to template the ligation of the released monomers into circles. Cleavage of an RCP at a restriction cleavage site typically generates linear oligonucleotide molecules with sequences at their 5' and 3' ends which are complementary to the sequence of the uncleaved restriction oligonucleotide used to create the restriction cleavage site. The 5' and 3' ends of the monomers may therefore hybridize to uncleaved restriction oligonucleotides present in the sample/reaction mixture, and be circularized by template-mediated ligation in a manner akin to the circularization of padlock probes upon binding to their respective target nucleic acid sequences. In other words, in certain embodiments a restriction oligonucleotide may be used both to generate a restriction cleavage site and as a ligation template for circularizing the RCA monomers following cleavage of the first RCP. Thus, a restriction oligonucleotide may be added to the sample during any of steps (a)-(d) of the method of the invention, and may template the ligation (circularization) of monomers into circles. Optionally, and as described below, the same restriction oligonucleotide may also prime a second and/or further RCA reaction.

The restriction oligonucleotides may preferably be added in excess, i.e. may be added a level greater than is required to hybridize to the first RCP, in order to allow the restriction oligonucleotide to create restriction cleavage sites in second or subsequent generation RCPs, to template the circularization of monomers in a C2CA reaction, and/or act as primers for second and/or further RCA reactions.

Thus, in a particularly preferred embodiment of the present invention, the first RCP may be amplified, wherein the amplification comprises:
  (i) if the first or previous RCP has not been monomerised, hybridizing the restriction oligonucleotide to the RCP at the sequence which is complementary or homologous to the RO sequence of the padlock probe, thereby to create a cleavage site in each monomer, and wherein the cleavage step (d) results in the cleavage of the concatemeric RCP into monomers;
  (ii) allowing both ends of the monomers to hybridize to uncleaved restriction oligonucleotide, ligating the hybridized ends to circularise the monomers thereby forming a secondary RCA template and performing a second RCA reaction using the secondary RCA template to form a second RCA product; and
  (iii) optionally repeating steps (i) and (ii) one or more times.

In a particular embodiment, amplification comprises a first, second and third RCA reaction.

The method of the present invention provides particular advantages when C2CA is used to amplify the product of an RCA reaction. As noted above, an unligated padlock probe may bind to an RCP and prime an extension reaction using the RCP as an extension template. Use of padlock probes which comprise an analyte-specific reporter sequence 3' to the restriction oligonucleotide sequence (e.g. as performed in the multiplexed detection methods of the prior art identified above), may result in the formation of an extension product in this way in which the analyte-specific reporter sequence of the padlock probe is situated 3' to the 5'-most restriction oligonucleotide sequence in the extension product thus formed. In C2CA, following restriction cleavage, the resulting monomers are circularized by hybridization of sequences at their 3' and 5' ends to a circularization template (a linear oligonucleotide). Thus, according to the methods of the prior art, the analyte-specific reporter sequence arising from the unligated padlock probe would be provided in a monomer which may be circularized by hybridization of sequences at its 5' and 3' ends to the same hybridization template that would be used to circularise the monomers created from cleavage of the linear RCA product. In this way, an RCA template containing the complement of the analyte-specific reporter sequence of the unligated padlock probe which bound to the RCP and primed the extension reaction may be formed. This RCA template would be amplified in a second or further RCA reaction, and will thus indicate the presence of an analyte which is not present in the sample. However, advantageously, in the methods of the present invention this may be avoided when performing a C2CA reaction, as during the restriction cleavage step the analyte-specific reporter sequence of the unligated padlock probe is 5' to the 5'-most restriction cleavage site of any extension product, and thus may be removed in the restriction cleavage step (i.e. it is provided in the partial monomer as described above, and thus does not comprise a sequence at its 5' end that would allow circularization to take place). Thus, this sequence is not provided in an RCA template for generation of a further RCP, and thus the problem of amplification of the incorrect analyte-specific reporter sequence in C2CA may be avoided. This particular benefit of the present invention is shown in FIG. 1, as described above.

In particular embodiments of the present invention wherein one or more rounds of C2CA is performed, the first RCP may be cleaved to reduce the size of the monomer as compared to the monomer in the first RCP, e.g. as described in WO2015/079042, which is hereby incorporated by reference in its entirety. In this way, a second RCA reaction using an RCA template that is smaller than the template used in the first RCA reaction may be performed.

The size of the monomer in the first RCP is reduced in these methods by cleaving the monomer two or more times, i.e. at two or more different positions within a monomer, thus resulting in the formation of two or more separate nucleic acid molecules per monomer of the first RCP. Thus, cleavage step (d) may comprise cleaving the first RCP at two or more positions within each monomer. In certain embodiments, the padlock probe may therefore be provided with two or more restriction oligonucleotide (RO) sequences. Restriction cleavage sites may be created by the addition of restriction oligonucleotides, and/or the padlock probe may comprise a RO sequence and a sequence complementary to the RO sequence, such that a stem-loop structure is created comprising a double-stranded restriction cleavage site. In the methods of WO2015/079042, formation of second RCA templates (i.e. the templates which are reduced in size relative to the first RCA templates) optionally comprises separating (i.e. removing or discarding) the portion of each monomer unit which is not incorporated into a second RCA template (i.e. the remainder of each monomer). The methods of the present invention require that the analyte-specific reporter sequence is retained in subsequent rounds of RCA in the C2CA reaction, so that the analyte of the assay may ultimately be detected.

Thus, according to these embodiments of the present invention, the analyte-specific reporter sequence is situated 5' to the 5'-most restriction oligonucleotide sequence within a padlock probe. Put another way, according to this embodiment of the invention, all of the restriction oligonucleotide sequences are located 3' to the analyte-specific reporter sequence. As discussed further below, it is not, however, precluded that other reporter sequences (which are not analyte-specific reporter sequences), for example detection oligonucleotide (DO) sequences which are discussed further below, may be situated 3' of a RO sequence.

In another embodiment the RCA reaction of step (c) may comprise a hyperbranched RCA reaction (HRCA) and amplification of the first RCP may occur as part of a HRCA reaction. Hyperbranched RCA (also known as strand displacement cascade reaction), e.g. as described in U.S. Pat. No. 6,183,960, is an isothermal amplification reaction which combines a linear rolling circle amplification reaction with strand displacement amplification (which may be performed subsequent to, or more preferably, simultaneously with, the first linear RCA reaction). Typically HRCA is performed by producing a first generation extension product produced using the RCP as an extension template, by providing a first (HRCA) primer complementary and capable of hybridizing to a portion of the RCP, and a second generation extension product using the first generation extension product as an extension template by providing a second (HRCA) primer complementary and capable of hybridizing to a portion of the first generation extension product (i.e. homologous to a portion of the RCP). 'Hyperbranching' is achieved by the first primer binding to the second generation extension product and forming a third generation extension product, and the second primer binding to the third generation extension product and forming a fourth generation extension product, and so on. In HRCA, primers may bind to the nascent growing 3' extension end of the previous generation extension product, and thus multiple primers may bind to a single extension product (owing to the concatemeric nature of the RCA product). Extension of a primer may partially displace downstream extension products from their extension template, thereby providing single-stranded nucleic molecules to which the next generation of primers may bind (to form the next generation of extension products).

Thus, in the methods of the present invention, the RCA reaction of step (c) may be an HRCA, wherein the linear RCA reaction takes place as part of the HRCA reaction and wherein the HRCA reaction takes place prior to step (d).

The first and second primers used in an HRCA reaction are or comprise sequences complementary to and homologous to (respectively) a portion of the RCA template that is to be subjected to HRCA, which allows the generation of hyperbranched extension products as described above.

The HRCA reaction may therefore comprise contacting the RCA template of step (b) with first and second HRCA amplification primers, wherein the first HRCA amplification primer is complementary and capable of hybridizing to a first portion of RCA template of step (b), and wherein the second HRCA amplification primer is homologous to the RCA template of step (b) and capable of hybridizing to a sequence which is complementary to a second portion of the RCA template, and wherein double-stranded extension products are formed, comprising a first strand which is complementary to at least part of the first RCP and a second strand which is homologous to at least part of the first RCP.

Ideally, the first and second portions of the RCA template of step (b) are not exactly the same, i.e. the amplification primers are not completely complementary to each other, to avoid the formation of primer dimers. However, in certain embodiments, it may be possible that the first and second amplification primers are partially complementary to each other, i.e. the first and second portions of the RCA template may be partially overlapping, as long as they retain the ability to bind to their respective target sequences and initiate extension. The HRCA amplification primers may be added before, during, or after step (b).

In the methods of the present invention, the primers used in an HRCA reaction may be specific for an amplification product (i.e. they may be complementary to and homologous to (respectively) a portion of the analyte-specific reporter sequence of the padlock probe. Alternatively, the primers used in an HRCA reaction may be common to two or more different amplification products, i.e. the same HRCA primers may be used to perform HRCA in the amplification of two or more different amplification products.

As well as "directed" HRCA primers designed to bind to specific or particular primer binding sites, random primers may be used. The use of random short oligonucleotide primers of, for example, 4 to 6 residues in length (e.g. hexamers) in amplification procedures is known in the art, and short (e.g. 4-6 mer) random HRCA primers may be used in the present methods.

Products of the HRCA reaction (i.e. the first and subsequent generation extension products) may be cleaved into monomers according to any of the methods described above. Preferably, as the extension products are double-stranded, cleavage does not require the addition of a restriction oligonucleotide. Thus, in certain embodiments of the present invention, the extension products may be cleaved into monomers, and the cleaved monomers may be detected in step (e).

Detecting the amplification products in step (e) may comprise the detection of further amplification products formed using the linear RCA product as an extension template.

As noted above, as well as C2CA or HRCA, other amplification methods may be used to amplify the first RCP, including non-RCA amplification methods. Such methods may include PCR or similar reactions. Thus, more generally, a step of amplifying the first RCP which is performed after step (c) may include an amplification reaction requiring at least two amplification primers, that is at least a first and second amplification primer, e.g. at least a forward and a reverse amplification primer. Such an amplification reaction may be performed as part of the detection step (in the sense that it is performed prior to the actual detection step (e), to provide amplicons which "report" the presence of the analyte, and which are detected to detect the analyte). Accordingly, such an amplification reaction may be performed using specific primers, e.g. analyte-specific primers. Suitable amplification methods include PCR and variants thereof, strand displacement amplification (SDA), helicase dependent amplification (HDA), loop-mediated isothermal amplification (LAMP) or the Smart Amplification Process (SMAP).

Whilst the use of such a further amplification reaction in the method does not require a cleavage step (and hence there is no requirement for the padlock probe to contain a RO sequence in addition to at least a first amplification primer binding site), as noted above it is advantageous for a cleavage step to be included.

Where there is not an RO sequence in the padlock probe, the probe must be designed such that there is not a second amplification primer binding site 5' to the analyte-specific reporter sequence. As explained above, in this way amplification of the analyte specific reporter sequence of an unligated padlock probe may be avoided, thereby reducing unwanted background (non-specific signal) in the assay.

Thus, for embodiments which include a further amplification step the padlock probe includes at least a first amplification primer binding site. In some embodiments the probe may also include a second amplification primer site, as long as this is not 5' of the analyte-specific reporter sequence. However, even for embodiments including a further amplification reaction requiring at least two primers, the padlock probe need not include a second or further primer binding site, as this can be generated in a complementary copy of the padlock probe (e.g. in the first RCP), or in an extension product of an unligated padlock probe (e.g. in an unligated padlock probe which has non-specifically hybridized to a first RCP and which has been extended using the first RCP as extension template)

As noted above, the location of the first amplification primer binding site in the padlock probe need not be specified and it may be situated 5' of, 3' of or within the analyte-specific reporter sequence. In one embodiment the first amplification primer binding site is located 3' or within the analyte-specific reporter sequence.

In a further embodiment the first and second amplification primer binding sites for the further amplification reaction are at least partially complementary to one another. In such an embodiment the padlock probe may comprise a first amplification primer binding site and does not comprise a second amplification primer binding site, the second amplification binding site being generated in a complementary copy of the padlock probe.

In another embodiment the padlock probe comprises distinct first and second amplification primer binding sites for a further amplification reaction, wherein the second amplification primer binding site in the probe is homologous to the second amplification primer and the second amplification primer hybridizes to a sequence complementary to the second amplification primer.

As noted above, an amplification reaction may be included as part of the detection process and hence may be performed in a specific way. Accordingly, in certain embodiments the two or more padlock probes used in the methods of the invention may each have a different first amplification primer binding site.

A method of the invention in which the padlock probes comprise at least a first amplification primer binding site for a further amplification reaction and optionally an RO sequence, may comprise the following steps:
(a) contacting the sample with the two or more padlock probes and allowing the probes to hybridize to their respective target sequences, if present;
(b) circularizing any padlock probe which has hybridized to its target nucleic acid sequence by ligation to form a rolling circle amplification (RCA) template;
(c) performing a linear RCA reaction using the RCA template(s) formed in step (b) to form first rolling circle amplification product(s) (RCP), wherein a first RCP is a concatemer comprising monomers which are complementary to the circularized padlock probe which templated its formation;
(d) optionally performing a restriction cleavage step during or after step (c), using a restriction enzyme capable of cleaving the restriction cleavage site, optionally together with a restriction oligonucleotide which is complementary to and capable of hybridizing to the restriction oligonucleotide (RO) sequence, to cleave the concatemeric first RCPs into monomers; and
(e1) subjecting the first RCP of step (c) or the cleaved monomers of the first RCP from step (d) to a further amplification reaction using at least first and second amplification primers; and
(e2) detecting the amplification product(s) of the amplification reaction of step (e1) to detect the analyte(s).

In such methods involving a further non-RCA amplification reaction as discussed above, in which at least two amplification primers are used (e.g. a PCR or similar reaction), the two amplification primers (and hence the corresponding primer binding site(s) in the padlock probe) will be designed to hybridize in such a manner as to be directed towards the analyte-specific reporter sequence (that is directed inwards, towards the analyte-reporter sequence). Thus, on a first RCP, or a monomer thereof, the first and second amplification primers may hybridize such that they flank the complement of the analyte-specific reporter sequence of the padlock probe. In the context of a first RCP this may be achieved by designing the amplification primers to bind either side of a ligation junction (i.e. the junction between the monomer units of the concatemer), such that amplification takes place over the ligation junction. Alternatively, amplification may take place using specific amplification primers, e.g. primers which are specific for different analyte-specific reporter sequences.

As noted above, in the methods of all aspects of the invention each padlock probe comprises an analyte-specific reporter sequence, which is identificatory of an analyte in the sample. The analyte-specific reporter sequence therefore identifies an analyte that is the subject of the methods of the present invention. In other words, the analyte is detected via or through detection of the analyte-specific reporter sequence. More specifically, detection of the analyte may comprise hybridization of the analyte-specific reporter sequence (or its complement) to an oligonucleotide specific for (i.e. complementary to) the analyte-specific reporter sequence or its complement. As discussed above and further below, such an oligonucleotide specific for (i.e. complementary to) the analyte-specific reporter sequence or its complement may be a detection probe (e.g. a detection oligonucleotide), a capture oligonucleotide (e.g. an array oligonucleotide (AO)) or a primer, particularly an amplification primer, and more particularly an analyte-specific primer.

The term "detecting" is used broadly herein to include any means of determining the presence or absence of the analyte (i.e. if it is present or not) or any form of measurement of the analyte. Thus the term "detecting" may alternatively be expressed as "assaying for"; it does not require that an analyte is actually detected. "Detecting" may include determining, measuring, assessing or assaying the presence or absence or amount or location of analyte in any way. Quantitative and qualitative determinations, measurements or assessments are included, including semi-quantitative. Such determinations, measurements or assessments may be relative, for example when two or more different analytes in a sample are being detected, or absolute. As such, the term "quantifying" when used in the context of quantifying a target analyte(s) in a sample can refer to absolute or to relative quantification. Absolute quantification may be accomplished by inclusion of known concentration(s) of one or more control analytes and/or referencing the detected level of the target analyte with known control analytes (e.g. through generation of a standard curve). Alternatively, relative quantification can be accomplished by comparison of detected levels or amounts between two or more different target analytes to provide a relative quantification of each of the two or more different analytes, i.e., relative to each other. As noted above, although it is included that the detection may occur in the same reaction mixture or same reaction vessel for all padlock probes, in some embodiments detection may involve carrying out separate, parallel detection reactions or detection procedures, and this may involve performing separate amplification reactions in parallel.

The analyte-specific reporter sequence, or indeed any other reporter sequence present in the padlock probe, or its complement may be a sequence which may be detected by any means, e.g. by hybridizing the amplification product to a detectable (i.e. directly or indirectly signal giving, e.g. labelled) complementary "detection oligonucleotide) or by hybridizing to a complementary capture oligonucleotide, which may be used to immobilise the reporter sequence or its complement to a solid phase as part of a detection process. For example, a reporter sequence or its complement may be used to attach the amplification product to a solid support in an addressable manner, which allows the amplification product, and hence the padlock probe which generated it, and thus the analyte, to be identified. This may for example comprise hybridizing the amplification product to an addressable array. Still further, the amplification product (e.g. a first RCP or a cleavage product thereof) may be hybridized to an amplification primer.

One or more reporter sequences may be used for detection. In certain preferred embodiments, detection involves both a capture (e.g. array hybridization) and a subsequent detection step. Thus the padlock probe may comprise a reporter sequence which is a detection oligonucleotide sequence (which, or the complement of which, may hybridize to a detection oligonucleotide) and/or a reporter sequence which is a capture (e.g. array) oligonucleotide sequence (which, or the complement of which, may hybridize to a capture (e.g. array oligonucleotide) sequence. The capture step may be performed in an analyte-specific manner, and may be followed by a non-analyte specific (i.e. general, or universal, or common) detection step, to detect the amplification products which have been captured in an analyte specific manner. In a particular embodiment, the analyte-specific reporter is accordingly a capture (e.g. array) oligonucleotide sequence. In such an embodiment, the padlock probe may further comprise a further reporter sequence which is a detection oligonucleotide sequence, which may or may not be analyte- or target-specific. Thus the detection oligonucleotide sequence may be common to all the padlock probes.

Accordingly, in certain embodiments of the present invention, detection may comprise detecting the hybridization of a detection oligonucleotide to the amplification product. Such a detection oligonucleotide may comprise one or more labels as described in greater detail below, e.g. one or more radiological or spectrophotometric, e.g. colorimetric or fluorescent labels. Detection of the amplification product may thus comprise detection of the binding of a labelled detection oligonucleotide to the amplification product. The amplification product may therefore comprise a sequence that is capable of hybridizing to a detection oligonucleotide in order for detection to take place.

In certain embodiments of the present invention, this may be the analyte-specific reporter sequence, i.e. the analyte-specific reporter sequence (or its complement) may be capable of hybridizing to a detection oligonucleotide in order for the amplification product to be detected. Thus, in the methods of the present invention, the analyte-specific reporter sequence may be a detection oligonucleotide (DO) sequence, wherein the detection oligonucleotide sequence or its complement is capable of hybridizing to an optionally labelled detection oligonucleotide, and the hybridization of the detection oligonucleotide is detected to detect the amplification product.

In other embodiments, a sequence other than the analyte-specific reporter sequence may be capable of hybridizing to a detection oligonucleotide in order for the amplification product to be detected, e.g. another (e.g. second) reporter sequence.

Thus, in certain embodiments, a reporter sequence may be a detection oligonucleotide (DO) sequence, and detecting the amplification product may comprise detecting the hybridization of a detection oligonucleotide to the detection oligonucleotide sequence (or its complement). Preferably in such embodiments, different amplification reagents may be distinguished, separated or isolated in some way (e.g. using the analyte-specific reporter sequence) in order to allow different amplification products to be detected.

In a preferred embodiment, the amplification product may be cleaved into monomers prior to detection. In such an embodiment, the padlock probe may comprise a detection oligonucleotide sequence (DO), and thus the resulting monomers may comprise a detection oligonucleotide (DO) sequence or its complement. Detection of the amplification product may therefore comprise contacting the monomers with an optionally labelled detection oligonucleotide complementary to and capable of hybridizing to the detection oligonucleotide sequence or its complement, and detecting the hybridization of the detection oligonucleotide to the detection oligonucleotide sequence to detect the amplification product.

As described in greater detail below, in certain embodiments, detection may be performed on a solid phase (this term is used interchangeably with "solid support"), i.e. the amplification products may be bound to a solid phase prior to or during detection step (e) in order to allow detection to take place. This may take place by binding of the amplification product to oligonucleotides immobilized to a solid phase either by the analyte-specific reporter sequence, or by another sequence (e.g. a further reporter sequence) within the amplification product.

In certain embodiments, the amplification products may be bound to a solid phase by the analyte-specific reporter sequence (or its complement) present in the amplification products. Thus, the analyte-specific reporter sequence or its complement may be capable of hybridizing to an oligonucleotide immobilized to a solid phase, e.g. an oligonucleotide in an array (an array oligonucleotide). In this way, different amplification products arising from padlock probes comprising different analyte-specific reporter sequences may be detected simultaneously in an array. The analyte-specific reporter sequence may therefore be an array oligonucleotide (AO) sequence, wherein the array oligonucleotide sequence or its complement is capable of hybridizing to an array oligonucleotide in an array.

In further embodiments, solid phase detection may require cleavage of the amplification products prior to detection (i.e. in cleavage step (d)), and the resulting monomers may be bound to a solid phase for detection. As described above, monomers formed in this way comprise the analyte-specific reporter sequence of the padlock probe which templated the formation of the first RCP (or its complement), and thus the cleaved monomers may be detected. In such embodiments, detecting the amplification product comprises contacting the monomers with an oligonucleotide immobilized to a solid surface, wherein the oligonucleotide is capable to hybridizing to the analyte-specific reporter sequence or its complement. In such embodiments, the analyte-specific reporter sequence may be an array oligonucleotide (AO) sequence.

In still further embodiments the analyte-specific reporter may be, or may comprise, a binding site for an amplification primer. Thus, amplification primers may be used to detect a RCP which are specific for different analyte-specific reporter sequences in different padlock probes. In this way it may be detected whether or not a given padlock probe has bound to its target and been ligated and amplified by detecting whether or not an amplification product has been generated and may be detected from the specific amplification primers. In other words it may be detected which specific amplification primers give rise to detectable amplification products. Advantageously, in such a format the amplification reactions using specific amplification primers may be performed and detected separately, e.g. in separate reaction vessels or chambers.

In any of the embodiments of the present invention, the padlock probes may comprise additional reporter sequences in addition to the analyte-specific reporter sequence. The padlock probes may therefore comprise an analyte-specific reporter sequence and at least one further reporter sequence.

The further reporter sequence may be common to some, or more preferably to all of the padlock probes.

In preferred embodiments, the amplification product may be bound to a solid surface, and detection may comprise detecting the hybridization of the amplification product to the solid support. Thus, the amplification product may comprise two separate sequences, wherein one sequence allows the amplification product to be bound to a solid surface, and the other sequence is capable of hybridizing to a detection oligonucleotide to allow detection of the amplification product. In particular, the two sequences may be an analyte-reporter sequence and at least one further reporter sequence as hereinbefore described.

In a particularly preferred embodiment, the amplification product may bind to an oligonucleotide immobilized at a solid phase by the analyte-specific reporter sequence, and may bind to an optionally labelled detection oligonucleotide by a further reporter sequence. Thus, the padlock probes may comprise an analyte-specific reporter sequence and at least one further reporter sequence, wherein the analyte-specific reporter sequence is an array oligonucleotide or wherein the analyte-specific reporter sequence or its complement is capable of hybridizing to an oligonucleotide immobilized on a solid surface, and wherein the further reporter sequence is a detection oligonucleotide sequence.

The further reporter sequences preferably do not overlap with the analyte-specific reporter sequences within a padlock probe, thereby to enable separate oligonucleotides to hybridize to each sequence independently once an amplification product has been formed. In preferred embodiments, the analyte-specific reporter sequence and at least one further reporter sequences are separate. Indeed, in preferred embodiments, further reporter sequences provided within a padlock probe are positioned such that following restriction cleavage (and removal of any sequence 5' to the restriction cleavage site), the further reporter sequence is not removed simultaneously with (i.e. as part of the same partial monomer with) the analyte-specific reporter sequence of an unligated padlock probe. Thus, in certain embodiments, the analyte-specific reporter sequence and at least one further reporter sequence are on opposite sides of the restriction oligonucleotide sequence, such they are separated upon cleavage.

In another embodiment the restriction oligonucleotide sequence and the further reporter sequence may overlap. The further reporter sequence may therefore be at least partially comprised within, or overlap, the restriction oligonucleotide sequence. In yet further embodiments, the detection oligonucleotide sequence may be a part of the restriction oligonucleotide sequence.

The products of the RCA reaction (i.e. at least the product of a linear RCA reaction) may therefore be detected using any convenient protocol, where in a preferred embodiment the particular protocol employed may detect the RCA product by detecting the complement of the analyte-specific reporter sequence within the RCA product (optionally following further amplification of the products of the RCA reaction), depending on the design (i.e. the domain organisation of the padlock probe, or the order in which the respective sequences are provided within the padlock probe). For example, the first RCP may be detected directly, e.g. the concatemer may be cleaved to generate monomers which may be detect using gel electrophoresis or on a solid phase e.g. on an array, or by hybridizing labelled detection oligonucleotides that hybridize to the complement of the analyte-specific reporter sequence in the RCA product. Alternatively, the first RCP may be detected indirectly, e.g. the product may be amplified (e.g. following one or more rounds of C2CA, or following PCR) and the amplification products may be detected.

Padlock probes comprising an analyte-specific reporter sequence and at least one further reporter sequence may therefore be provided in a number of preferred designs, depending on the particular amplification and/or detection methods that are to be used in the detection of the analyte.

For example, in preferred embodiments of the present invention, detection takes place on a solid phase. In such embodiments, the amplification product binds to an oligonucleotide immobilized to a solid phase (e.g. array oligonucleotides as described above), and detection oligonucleotides may bind to the amplification product. In certain such embodiments the array oligonucleotide (AO) sequence and detection oligonucleotide (DO) sequence may be separated by the restriction oligonucleotide (RO) sequence, or the array oligonucleotide (AO) sequence is separate from the detection oligonucleotide (DO) sequence, which sequence may be partially or fully overlapping with the restriction oligonucleotide (RO) sequence, such that in the restriction cleavage step the array oligonucleotide sequence (AO) is removed (i.e. separated) from the detection oligonucleotide (DO) sequence. However, it is not necessary for AO and DO sites to be separated, for example where stringent washing steps to remove unligated padlock probes are included. Various different possible arrangements of the AO, RO and DO sequences are discussed further below. In this context, an AO sequence instead be, or may comprise, an alternative analyte-specific reporter sequence, e.g. an amplification primer binding site.

Use of probes according to the above designs may be of particular benefit where an unligated padlock probe has bound to an RCP and primed an extension reaction using the RCP as an extension template. Multiplexed detection methods described in the prior art identified above use padlock probes which comprise an analyte-specific reporter sequence (i.e. an array oligonucleotide AO sequence) 3' to the restriction oligonucleotide sequence. Any extension product formed from such an unligated padlock probe which uses an RCP as a template for extension will therefore comprise the analyte-specific reporter sequence of the padlock probe situated 3' to the 5'-most restriction oligonucleotide sequence in the extension product. Following restriction cleavage, the monomer comprising this analyte-specific oligonucleotide sequence (particularly an array oligonucleotide sequence) will also comprise a detection oligonucleotide sequence, and will therefore be detected, thus indicating the presence of an analyte which is not present in the sample. By contrast, use of padlock probes according to any of the specific embodiments described above, this may be avoided, as during the restriction cleavage step, the analyte-specific reporter sequence of the unligated padlock probe (i.e. the array oligonucleotide sequence) is 5' to the 5'-most restriction cleavage site of the extension product, and thus is removed in the restriction cleavage step (i.e. it is provided in the partial monomer). The detection oligonucleotide sequence deriving from the unligated padlock probe, being 3' to, or within the restriction oligonucleotide sequence, is thereby separated from the analyte-specific reporter sequence of the unligated padlock probe, and thus this analyte-specific reporter sequence is not detected in detection step (e). This is illustrated in FIGS. 2A and 2B.

Thus, in certain embodiments, where the padlock probe comprises an analyte-specific reporter sequence and a further reporter sequence, the padlock probe may comprise, in the order 5' to 3':

i) an array oligonucleotide sequence (AO), restriction oligonucleotide sequence (RO), detection oligonucleotide sequence (DO);
ii) an array oligonucleotide sequence (AO), restriction/detection oligonucleotide sequence (RO/DO); or
iii) an array oligonucleotide sequence (AO), detection oligonucleotide sequence (DO), restriction oligonucleotide sequence (RO).

(i) and (ii) are preferred. In the context of (ii) it should be noted that in the partially overlapping RO/DO sequence the DO sequence is 3' of the RO site.

As described above, use of padlock probes which comprise the analyte-specific reporter sequence 5' to the restriction cleavage site ensures that the analyte-specific reporter domain of unligated padlock probes cannot be included in second or subsequent rounds of RCA, as the partial monomer at the 5' end of any extension product that is formed does not comprise sequences at both its 5' and 3' ends which allow it to be circularized, and thus the template for a further round of RCA. In such embodiments, amplification of the 'correct' monomers in a subsequent RCA reaction will increase the signal detected sufficiently that any partial monomers formed which comprise both an array oligonucleotide sequence and a detection oligonucleotide sequence will not significantly interfere with detection. Thus, in such embodiments, a padlock probe which comprises an adjacent array oligonucleotide sequence and a detection oligonucleotide sequence may be used. Although less preferred, such an arrangement may also be used in other assay formats, e.g. using HRCA.

Preferably, a signal producing system that is specific for the RCA product, as opposed to nucleic acid molecules in general, may be employed to detect the amplification. In these embodiments, the signal producing system may include a probe nucleic acid or oligonucleotide that specifically binds to a sequence found in the RCA product (i.e. a reporter sequence), where the probe nucleic acid/oligonucleotide may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probe nucleic acids (i.e. detection probes) include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the detection oligonucleotides are labelled with "energy transfer" labels. As used herein, "energy transfer" refers to the process by which the fluorescence emission of a fluorescent group is altered by a fluorescence-modifying group. Energy transfer labels are well known in the art, and such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Further examples of detection probes include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference).

Thus, determining the presence of the amplification products may be achieved using any convenient protocol. The reaction mixture may be screened etc. (i.e., assayed, assessed, evaluated, tested, etc.) for the presence of any resultant amplification products in order to detect the presence of the analyte in the sample being assayed. The particular detection protocol may vary depending on the sensitivity desired and the application in which the method is being practiced.

In some embodiments detection probes (i.e. detection oligonucleotides) as discussed above, e.g., fluorescently labelled probes, molecular beacons (as described above), TaqMan® probes etc. may be employed to detect to the presence of the amplification product, where these probes are directed to a sequence (i.e. the analyte-specific reporter sequence or its complement) that is present in the amplification product.

The reaction mixture prepared in this detection step of the subject methods may further include an aqueous buffer medium that includes a source of monovalent ions, a source of divalent cations and a buffering agent. Any convenient source of monovalent ions, such as KCl, K-acetate, NH4-acetate, K-glutamate, $NH_4Cl$, ammonium sulphate, and the like may be employed. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, although higher or lower amounts may be used and may depend on the type of reaction. For instance, for PCR the amount of $Mg^{2+}$ present in the buffer may be about 1.5 mM, whereas for RCA, the amount of $Mg^{2+}$ present in the buffer may about 10 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

The next step in the subject methods is signal detection from the labelled amplification product(s), where signal detection may vary depending on the particular signal producing system employed. In certain embodiments, merely the presence or absence of detectable signal, e.g., fluorescence, is determined and used in the subject assays, e.g., to determine or identify the presence or absence of the amplification product(s) (and hence the analyte(s)). Depending on the particular label employed, detection of a signal may indicate the presence or absence of the amplification product(s).

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or, for example where the sample is a tissue sample on a microscope slide, fluorescence may be detected using a fluorescence microscope. Fluorescence is suitably monitored using a known fluorimeter. The signals from these devices, for instance in the form of photomultiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

The data generated as described above can be interpreted in various ways. in its simplest form, an increase or decrease in fluorescence from the sample in the course of or at the end of the amplification reaction is indicative of an increase in the amount of the target analyte present in the sample, e.g. as correlated to the amount of RCA product detected in the reaction mixture, suggestive of the fact that the amplification reaction has proceeded and therefore the target analyte was in fact present in the initial sample. Quantification is also possible by monitoring the amplification reaction throughout the amplification process. Quantification may also include assaying for one or more nucleic acid controls in the reaction mixture, as described above.

In this manner, a reaction mixture may readily be screened (or assessed or assayed etc.) for the presence of RCA or other amplification product, and hence of target analyte(s), e.g. nucleic acid analytes. The methods are suitable for detection of a single target analyte (using multiple (i.e. two or more) padlock probes as well as multiplex analyses in which two or more different target analytes are assayed in the sample. In these latter multiplex situations, the number of different probes that may be employed for detection may typically range from about 2 to about 20 or higher, e.g., as up to 100 or higher, 1000 or higher, etc. wherein the multiple analytes in a sample may be detected in parallel or sequentially.

The analysis of many analytes simultaneously and in a single reaction using several different probes may be enhanced by the increased sensitivity, and in certain embodiments also increased specificity, which may be obtained using the methods of the invention. Each analyte may be detected via a distinct first RCA template that produces a RCA product that can be used to determine the presence or absence, quantity and/or location of the analytes being assayed. The RCA product may be detected using any of the well-established methods for analysis of nucleic acid molecules known from the literature including liquid chromatography, electrophoresis, mass spectrometry, microscopy, real-time PCR, fluorescent probes, microarray, colorimetric analysis such as ELISA, flow cytometry, mass spectrometry (CyTOF) etc.

Preferably, the amplification products may be detected using a solid phase, e.g. by using an array or a microarray. Such an array may be any type of DNA microarray, and may include a planar array (both porous and non-porous) and bead arrays, as may be ordered or non-ordered arrays. Example array formats known in the art include a standard planar microarray (e.g. as provided by Affymetrix), and bead arrays (e.g. Luminex (R&D Systems) or a BeadArray (Illumina)).

Conventional planar arrays comprise a series of orderly microscopic "spots", (features) each comprising multiple copies of an oligonucleotide attached to a surface, such as a glass, plastic or silicon biochip. Multiple (e.g. up to thousands) of such spots or features may be provided on a single chip, each placed in a known location on a single microarray. Hybridization of a target oligonucleotide (i.e. the amplification products in the present invention) to an immobilized oligonucleotide is typically detected by scanning the microarray to detect a signal arising from each of the spots on the array.

An alternative to a planar array is a bead array, in which a collection of microscopic polystyrene beads is provided, each having a specific probe and a ratio of two or more dyes, which do not interfere with the fluorescent dyes used on the target surface.

The method of the present invention may be used to detect more than one different analyte in a sample, for example 2, 3, 4, 5, 6, 7, 8, 9, 10 or more different analytes in a sample. Thus, 15, 20, 25, 30, 40, 50, 60, 70, 80, 90 or 100 or more different analytes may be detected using the method of the present invention. More specifically, however, the method of the present invention may be used to detect more than one different target nucleic acid sequence, i.e. using two or more different padlock probes. As described above, the detection of a target nucleic acid sequence may be a proxy for the detection of an analyte, and detection of two or more different target nucleic acid sequences may each indicate the presence of the same analyte (including the presence of one of a group of analytes) in the sample.

The 5' and 3' ends of a padlock probe which are complementary to a target nucleic acid molecule may be any suitable length that allows the respective end regions of the padlock probe to hybridize in a specific manner to complementary sequences on the target nucleic acid sequence. For example, each end region may be 6-20 nucleotides in length. A minimum size of 6 nucleotides is selected to ensure specificity of binding. Thus, preferably the size range of each of the end regions may be 6-20, 6-19, 6-18, 6-17, 6-16, 6-15, 6-14, 6-13, 6-12, 6-11 or 6-10 nucleotides in length. The length of each end region of a probe may be the same or different, and thus for example a probe may have target-complementary regions of 6+6, 6+7, 7+7, 6+8, 7+8, 8+8, 8+9, 7+9, 9+9, 10+9, 10+10, 10+11, 11+11, 11+12, 12+12 etc., i.e. any combination of any integers within the above-noted ranges.

Thus, the length of the hybridized region may be 12-32, more particularly 12-40 nucleotides, more particularly 12-36, 12-32 or 12-30, 12-28, 12-26, 12-24, 12-23, 12-22, 12-21, 12-20, 12-19, 12-18, 12-17, 12-16, 10 13-30, 13-28, 13-26, 13-24, 13-23, 13-22, 13-21, 13-20, 13-19, 13-18, 13-17, 13-16, 14-30, 14-28, 14-26, 14-24, 12-23, 14-22, 14-21, 14-20, 12-19, 14-18, 14-17, 14-16, 15-30, 15-28, 15-26, 15-24, 15-23, 15-22, 15-21, 15-20, 15-19, 15-18, 15-17, or 15-16 nucleotides.

The 5' and 3' ends of the padlock probe may hybridize to a sequences in a target nucleic acid sequence directly adjacent to each other such that they may be directly ligated, thereby to circularise the padlock probe. The ends of the padlock probe may alternative hybridize to sequences in a target nucleic acid sequence which are not directly adjacent, such that ligation is indirect. Thus where the ligation of the probe ends is indirect, the free ends hybridize to the target with a space in between which is filled by a "gap" oligonucleotide such that each free end is ligated to one end of the gap oligonucleotide. Alternatively, the space in between the free ends may be "filled-in" by extending the free 3' end, e.g. in a polymerase reaction, using the target nucleic acid molecule as an extension template. Once the free 3' end has been extended to be adjacent to the free 5' end, the two ends may be joined by a ligation reaction. Accordingly, the total hybridized regions mentioned above may be made up of the probe target complementary regions and optionally the gap-fill sequences.

It will be understood therefore that in the gap-fill embodiments of the invention where the probe ends are ligated indirectly to one another, the gap may be from 1-20 nucleotides long, e.g. 1-19, 1-18, 1-15, 1-12, 1-10, 1-8, 1-7, 1-6, 1-5, 1-4, or from 2, 3, 4, 5, or 6 to any of the upper limits of the above-noted ranges. The term "hybridization" or "hybridizes" as used herein refers to the formation of a duplex between nucleotide sequences which are sufficiently complementary to form duplexes via Watson-Crick base pairing. Two nucleotide sequences are "complementary" to one another when those molecules share base pair organization homology. Hence, a region of complementarity refers to a portion of a nucleic acid molecule that is capable of forming an intra- or intermolecular duplex, i.e. either a duplex within the same molecule (a hairpin or stem-like structure) or a duplex with a different molecule. These terms are also used to refer to base pair interactions which are analogous to Watson-Crick base pairing, including Hoogsteen base pairing which is a rarely observed variation of base pairing which also allows for a third strand to wind around a double-helix assembled in a Watson-Crick pattern to form a triplex.

As is known in the art, in template-directed ligation ligases catalyse the formation of a phosphodiester bond between juxtaposed 3'-hydroxyl and 5'-phosphate termini of two immediately adjacent nucleic acids when they are annealed or hybridized to a third nucleic acid sequence to which they are complementary (i.e. a ligation template). Any convenient ligase may be employed, where representative ligases of interest include, but are not limited to: temperature sensitive and thermostable ligases. Temperature sensitive ligases include, but are not limited to, bacteriophage T4 DNA ligase, bacteriophage T7 ligase, and E. coli ligase. Thermostable ligases include, but are not limited to, Taq ligase, Tth ligase, Ampligase® and Pfu ligase. Thermostable ligase may be obtained from thermophilic or hyperthermophilic organisms, including but not limited to, prokaryotic, eukaryotic, or archael organisms. Certain RNA ligases may also be employed in the methods of the invention.

A suitable ligase and any reagents that are necessary and/or desirable may be combined with the reaction mixture and maintained under conditions sufficient for ligation of the hybridized oligonucleotides to occur. Ligation reaction conditions are well known to those of skill in the art. During ligation, the reaction mixture in certain embodiments may be maintained at a temperature ranging from about 4° C. to about 105° C., about 4 to about 80° C., such as about 10 to about 70° C., about 15 to about 60° C., typically such as from about 20° C. to about 37° C. for a period of time ranging from about 5 seconds to about 16 hours, such as from about 1 minute to about 1 hour. In yet other embodiments, the reaction mixture may be maintained at a temperature ranging from about 35° C. to about 45° C., such as from about 37° C. to about 42° C., e.g., at or about 38° C., 39° C., 40° C. or 41° C., for a period of time ranging from about 5 seconds to about 16 hours, such as from about 1 minute to about 1 hour, including from about 2 minutes to about 8 hours. Temperature ranges as discussed immediately above are generally suitable for mesophilic ligases (e.g., T4 ligase or E. coli ligase). For more thermostable ligases (e.g. Tth ligase, ampligase, Taq ligase etc.) higher temperatures may be used, in accordance with protocols and procedures well known in the art. In a representative but non-limiting embodiment, the ligation reaction mixture includes 50 mM Tris pH7.5, 10 mM $MgCl_2$, 10 mM DTT, 1 mM ATP, 25 mg/ml BSA, and T4 DNA ligase at 0.125 units/ml. In yet another representative embodiment, 2.125 mM magnesium ion, and 0.125 units/ml DNA ligase are employed. RNase inhibitor may additionally be included if RNA is targeted.

It will be evident that the ligation conditions may depend on the ligase enzyme used in the methods of the invention. Hence, the above-described ligation conditions are merely a representative example and the parameters may be varied according to well-known protocols. For example, a ligase that may be utilized in the methods of the invention, namely Ampligase®, may be used at temperatures of greater than 50° C. However, it will be further understood that the alteration of one parameter, e.g. temperature, may require the modification of other conditions to ensure that other steps of the assay are not inhibited or disrupted, e.g. binding of the probe to the target nucleic acid molecule. Such manipulation of RCA assay methods is routine in the art.

The primer for an RCA reaction comprises a region of complementary to a part of the RCA template, which forms a duplex that is sufficiently stable under the conditions of the assay to facilitate RCA template dependent extension of the primer. Similar considerations apply to other amplification primers. The primer will generally be at least 4 or 5 nucleotides in length, typically at least 6, 8 or 10, usually at least 15 or 16 nucleotides in length and may be as long as 30 nucleotides in length or longer, where the length of the primer will generally range from 5 to 50 nucleotides in length, e.g. from 6, 8 or 10 to 50, 40, 30 or 20, usually from about 10 to 35 nucleotides in length. Where a primer is designed to bind specifically to a particular amplification primer binding site it will generally be longer (e.g. at least 8 nucleotides in length. However, in some embodiments, a random primer may be used, as noted above.

A primer (or more particularly one or more primers) for the RCA reaction of step (c) may be added to the sample or reaction mixture at any convenient time, e.g. before or during step (c). It (or they) may be added in or after step (a), or in or after step (b) or during step (c).

In certain embodiments, the primer for an RCA reaction may be a restriction oligonucleotide, i.e. an oligonucleotide complementary to a restriction oligonucleotide (RO) sequence in a padlock probe. Uncleaved restriction oligonucleotides may hybridize to the circularized padlock probes via the restriction oligonucleotide (RO) sequence, thereby to act as a primer for rolling circle amplification.

As noted above, the methods of the present invention may be employed homogeneously (i.e. in solution) or heterogeneously, using a solid phase. The use of solid phase assays offers advantages, particularly for the detection of difficult samples: washing steps can assist in the removal of unligated molecules etc., inhibiting components, and analytes can be enriched from an undesirably large sample volume.

The manner or means of immobilization and the solid support may be selected, according to choice, from any number of immobilization means and solid supports as are widely known in the art and described in the literature. Thus the selected reagent or component for immobilization may be directly bound to the support (e.g. chemically cross-linked), it may be bound indirectly by means of a linker group, or by an intermediary binding group(s) (e.g. by means of a biotin-streptavidin interaction). Thus, a monomer unit or an RCA primer or product may be provided with means for immobilization (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support.

The solid support may be any of the well-known supports or matrices which are currently widely used or proposed for immobilization, separation etc. These may take the form of particles (e.g. beads which may be magnetic or nonmagnetic), sheets, gels, filters, membranes, fibres, capillaries, or microliter strips, tubes, plates or wells etc.

The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10, and e.g. not more than 6 μm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the analyte binding steps. This may be of particular benefit for lab-on-a-chip applications, as recently described for performing C2CA (Kümmermund et al. 2014. Lab Chip 14, 2983-2992).

In a further embodiment, the analyte itself may be immobilized (or immobilizable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilized on a microscope slide.

As noted above the above described methods for detecting the presence of one or more target analytes in a complex sample find use in a variety of different applications.

The subject methods may be used to screen a sample for the presence or absence of one or more target analytes in a sample or for quantifying the amount of one or more target analytes in a sample.

In a further aspect, the present invention provides a panel of padlock probes for use in multiplexed detection of an analyte in a sample, the panel comprising at least two padlock probes, wherein each padlock probe comprises 5' and 3' end sequences capable of hybridizing to a different target nucleic acid sequence, which target sequence is either part of the analyte or is indicative of the presence of the analyte in the sample, such that upon the hybridization the ends of the padlock probe are brought into juxtaposition, directly or indirectly, for ligation to circularise the padlock probe, and wherein each padlock probe comprises, between its 5' and 3' ends, at least one reporter sequence, at least one of the reporter sequences being an analyte-specific reporter sequence and either (i) a restriction oligonucleotide (RO) sequence capable of hybridizing to a complementary sequence to create a restriction cleavage site, wherein the RO sequence is located 3' of the analyte-specific reporter sequence such that cleavage at the restriction cleavage site occurs 3' of the analyte-specific reporter sequence and allows the analyte-specific reporter sequence to be removed from the padlock probe, or (ii) a binding site for a first amplification primer, wherein the binding site may be present 5' of, 3' of, or within the analyte-specific reporter sequence but wherein where the first amplification primer binding site is present, the padlock probe does not comprise a binding site for a second amplification primer 5' of the analyte-specific reporter sequence, or both (i) and (ii).

More particularly in one embodiment of this further aspect the present invention provides a panel of padlock probes for use in multiplexed detection of an analyte in a sample, the panel comprising at least two padlock probes, wherein each padlock probe comprises 5' and 3' end sequences capable of hybridizing to a different target nucleic acid sequence, which target sequence is either part of the analyte or is indicative of the presence of the analyte in the sample, such that upon the hybridization the ends of the padlock probe are brought into juxtaposition, directly or indirectly, for ligation to circularize the padlock probe, and wherein each padlock probe comprises, between its 5' and 3' ends, a restriction oligonucleotide (RO) sequence capable of hybridizing to a complementary sequence to create a restriction cleavage site and at least one reporter sequence, at least one of the reporter sequences being an analyte-specific reporter sequence, and the RO sequence is situated 3' of the analyte-specific reporter sequence such that cleavage at the restriction cleavage site occurs 3' of the analyte-specific reporter sequence and allows the analyte-specific reporter sequence to be removed from the padlock probe.

The panel of padlock probes of the present invention may be suitable for performing any of the methods hereinbefore described.

The methods described above may be modified to use, in place of single target-specific probe, a set of two or more padlock probes which each have the same target specific sequences, i.e. wherein the padlock probes in a set are each capable of hybridizing to the same target nucleic acid sequence. This may help to increase specificity in methods where the concentration or amount of analytes (and hence of target sequences) may vary across a wide range. In such a situation a very sensitive method of detection, such as is permitted by the methods of the present invention coupled with the large range of input target amounts increases the risk of background signals, particularly where one of the targets is present in large amounts. By using such sets of padlock probes background signals may be reduced, or more particularly signal to noise (S/N) ratios may be increased. Such a modified method may further allow the dynamic range of the detection assay to be enhanced in respect of each individual analyte. Methods for increasing the dynamic range of a detection method comprising padlock probes are known in the art, e.g. as taught in WO 2012/04931.

Thus, in yet another aspect, the present invention provides a multiplexed method of detecting an analyte in a sample using two or more sets of padlock probes wherein the padlock probes within each set comprise the same 5' and 3' end sequences capable of hybridizing to a target nucleic acid sequence and each set is capable of hybridizing to a different target nucleic acid sequence, which target sequence is either part of the analyte or is indicative of the presence of the analyte in the sample, such that upon the hybridization the ends of the padlock probe are brought into juxtaposition, directly or indirectly, for ligation to circularise the padlock probe, and wherein each padlock probe comprises, between its 5' and 3' ends, a restriction oligonucleotide (RO) sequence capable of hybridizing to complementary sequence to create a restriction cleavage site and at least one reporter sequence, at least one such reporter sequence being an analyte-specific reporter sequence, and the RO sequence is located 3' of the analyte-specific reporter sequence such that cleavage at the restriction cleavage site occurs 3' of the analyte-specific reporter sequence, the method comprising:

(a) contacting the sample with the two or more sets of padlock probes and allowing the probes to hybridize to their respective target sequences, if present;
(b) circularizing any padlock probe which has hybridized to its target sequence by ligation to form a rolling circle amplification (RCA) template;
(c) performing a RCA reaction which comprises at least a linear RCA reaction using the RCA template(s) formed in step (b) to form first rolling circle amplification product(s) (RCP), wherein a first RCP is a concatemer comprising monomers which are complementary to the circularized padlock probe which templated its formation;
(d) during or after step (c), performing a restriction cleavage step using a restriction enzyme capable of cleaving the restriction cleavage site, optionally together with a restriction oligonucleotide which is complementary and capable of hybridizing to the RO sequence; and
(e) after step (d), detecting the amplification product(s) to detect the analyte(s);

wherein each set of padlock probes comprises at least two padlock probes, wherein each padlock probe in a set:
(i) comprises a different reporter sequence to any other padlock probe in the set and thereby generates a RCP that is distinguishable from the RCP generated by another padlock probe in the set, wherein the different reporter sequence is the analyte-specific reporter sequence or is a further, tag reporter sequence;
(ii) cannot interact with its target nucleic acid sequence simultaneously with another padlock probe in the set; and
(iii) is present in an amount capable of detecting the analyte at a range of concentrations that differs from the range of concentrations detectable by other padlock probes in the set.

The padlock probes may function to extend the dynamic range of detection, but it is not required that the dynamic range of detection for each separate analyte be increased.

It will therefore be seen that in this method, two or more padlock probes (the padlock probes of a set of padlock probes) may be provided which are capable of hybridizing to the same target nucleic acid molecule, and thus each target nucleic acid molecule may be detected by each of a set of two or more padlock probes. Thus, each set of padlock probes is capable of hybridizing to a different target nucleic acid sequence.

The dynamic range (DR or DNR) is the ratio between the smallest and largest possible values of a changeable (i.e. variable) quantity. The dynamic range of an analyte in a sample will depend on the nature of the sample, e.g. source and size, and the analyte, e.g. a DNA molecule from one pathogen may be present as a single copy in a sample, whereas there may be millions of copies of DNA molecules from other pathogens or cells in the same sample. This may especially be the case if growth of the pathogen has occurred before assaying for the presence of the DNA of one of the pathogens but not the other, such as may occur in a method which involves culture of a sample before microbial detection, which is typical of many methods and protocols for the detection of pathogens in clinical samples (including for example a method as described in WO 2015/189390). Thus, a single typical biological sample could encompass a dynamic range from a single molecule to a molar concentration, e.g. the receptor HER2 (Erbb2) can be present a quantities of up to 2,000,000 receptors per cell whereas a neighbouring cell can have as few as 10 receptors (or of course none at all), or a sample could contain 0.1 CFU/ml of e.g. *Candida albicans* and/or $10^9$ CFU/ml of *E. coli* and more importantly *E. coli* could also be present at a concentration of 1 CFU/ml. To be able to detect and quantify an analyte in a sample where the analyte could be present in such a range of concentrations would require a method capable of not reporting above 0.1 CFU/ml for one analyte, e.g. *C. albicans*, even in the presence of $10^9$ CFU/ml of another analyte, e.g. *E. coli*, while still the method would need to be sensitive enough to be able to report the analytes (here *C. albicans* and *E. coli*) when present in 1 CFU/ml with a DR of at least 1:200,000, i.e. a method capable producing a detectable signal for a single molecule, whilst also capable of producing a non-saturated signal in the presence of 2,000,000 molecules. A method with a dynamic range of less than 1,000 would not be useful for analysing different samples where the concentration of the analyte could range, e.g. from pM to nM, or nM or µM, or µM or mM etc.

In a situation where the expected concentration range of an analyte is unknown or the potential concentration range of the sample is broad, one option is to generate a serial dilution of the sample and/or the reagents (e.g. the padlock probes) and perform a variety of assays combining the various dilutions to determine the optimum conditions at which the analyte can be detected in the sample. This is can result in a large number of assays to be performed for a single analyte. Where the sample comprises more than one analyte of interest, the number of assays required can quickly escalate, particularly where the detection reagents for each analyte have different detection limits, e.g. if the detection reagents are antibodies with divergent binding affinities for their corresponding analytes. This may also preclude detecting the different analytes in a single assay and may make it impossible to detect an analyte in a rare or small sample, i.e. where there is an insufficient amount of the sample to perform multiple assays.

As noted above, advantageously, this modified method allows two or more different analytes, each present in the sample at a different copy number, to be more easily detected. For example, two analytes which are present in the sample at a larger range of concentrations that could be detected using the methods of the first aspect of the invention (i.e. the "unmodified" methods) may be detected simultaneously according to this aspect of the present invention. Thus, this aspect of the invention increases the functional dynamic range of the detection method as a whole, and may additionally extend the dynamic range of detection of each analyte therein.

Advantageously, this aspect of the present invention allows the dynamic range of detection to be increased without performing a serial dilution or detecting different analytes separately, i.e. in separate detection assays.

The two or more padlock probes in a set are provided at amounts capable of detecting the analyte at a range of concentrations that differs from the range of concentrations detectable by other padlock probes in the set. Put another way, the two or more padlock probes in a set are provided at different concentrations, such that the dynamic range at which the amplification product from any one of the padlock probes in a set may be detected is different from the dynamic range at which the amplification product from any other padlock probe in a set may be detected.

The analyte-specific reporter sequence in each padlock probe in a set may be different, in order to allow the analyte-reporter sequence from each padlock probe to be detected separately. However, each analyte-specific reporter sequence is specific to a particular analyte, as in the first aspect of the present invention. Thus, in this modified aspect of the present invention, two or more analyte-specific reporter sequences (provided in two or more padlock probes from a set of padlock probes) may be specific for a given analyte. (In this sense, 'analyte' takes the same meaning as in the first aspect of the invention.) The amplification product formed from each of the padlock probes may thus be detected as described above.

In a preferred embodiment, the amplification product arising from each of the padlock probes from a set formed in this way may be detected using detection oligonucleotides (i.e. the padlock probes may comprise a further reporter sequence, wherein the sequence is a detection oligonucleotide sequence. Preferably in such embodiments, the same detection oligonucleotide may be used to detect the amplification products formed from each of the padlock probes in a set.

In alternative embodiments, however, the analyte-specific reporter sequence in each padlock probe in a set may be the same, but each padlock probe in the set may comprise a different further reporter sequence (i.e. a different oligonucleotide sequence). In this way, a different detection oligonucleotide may be used to detect the amplification products from each of the padlock probes in a set. Thus, two or more different detection oligonucleotides, each capable of hybridizing to a different detection oligonucleotide sequence, may be used to detect amplification products formed in this way.

The same two or more detection probes may be used in the detection of two more analytes in a sample according to this aspect of the invention. Thus, a set of two or more padlock probes may be provided for each analyte, wherein each padlock probe in a set comprises the same analyte-specific reporter sequence, and wherein a first padlock probe from each set comprises a first detection oligonucleotide sequence, and a second or subsequent (i.e. third, fourth or fifth etc.) padlock probe from each set comprises a second or subsequent (i.e. third, fourth or fifth etc.) detection oligonucleotide sequence.

By way of representative example, if two sets of two padlock probes are provided to detect analytes Y and Z, probe set 1 may comprise probes A1 and B1, and probe set 2 may comprise probes A2 and B2. For each set, probe A may be provided at a concentration 10× greater than probe B. However, probes A1 and A2 may comprise the same detection oligonucleotide sequence (DO-A), and probes B1 and B2 may comprise the same detection oligonucleotide sequence (DO-B), such that DO-A (and thus the detection of the high concentration probes) is distinguishable from DO-B (for the detection of low concentration probes). In this way, one detection oligonucleotide may be used to detect the amplification products from all of the 'A' probes, and one detection oligonucleotide may be used to detect the amplification products from all of the 'B' probes. Analogously to as described above, two or more padlock probes from a set of padlock probes may have different AO sequences and thus two or more AO sequences may be specific for a given analyte, but will be contained in padlock probes used in different amounts.

Preferably, in such embodiments, the detection oligonucleotides for detecting the amplification products may be labelled. Preferably, the different detection oligonucleotides (i.e. for detecting a given detection oligonucleotide) are labelled differently, such that they may be independently detected (and thus that the amplification products for the same analyte may be differentiated).

According to yet another aspect of the invention, there is provided a panel comprising two or more sets of padlocks probes for use in multiplexed detection of an analyte in a sample, each set being capable of hybridizing to a different target nucleic acid sequence, and the padlock probes within each set comprising the same 5' and 3' end sequences capable of hybridizing to the same target nucleic acid sequence, wherein the target sequence is either part of the analyte or is indicative of the presence of the analyte in the sample, such that upon the hybridization the ends of the padlock probe are brought into juxtaposition, directly or indirectly, for ligation to circularise the padlock probe, and wherein each padlock probe comprises, between its 5' and 3' ends, a restriction oligonucleotide (RO) sequence capable of hybridizing to complementary sequence to create a restriction cleavage site and at least one reporter sequence, at least one such reporter sequence being an analyte-specific reporter sequence, and the RO sequence is located 3' of the analyte-specific reporter sequence such that cleavage at the restriction cleavage site occurs 3' of the analyte-specific reporter sequence and allows the analyte-specific reporter sequence to be removed from the padlock probe;

and wherein each set of padlock probes comprises at least two padlock, wherein each padlock probe in a set:
(i) comprises a different reporter sequence to any other padlock probe in the set and thereby generates a RCP that is distinguishable from the RCP generated by another padlock probe in the set, wherein the different reporter sequence is the analyte-specific reporter sequence or is a further, tag reporter sequence;
(ii) cannot interact with its target nucleic acid sequence simultaneously with another padlock probe in the set; and
(iii) is present in an amount capable of detecting the analyte at a range of concentrations that differs from the range of concentrations detectable by other padlock probes in the set.

In yet another aspect, the present invention provides a kit for use in a multiplexed method of detecting an analyte in a sample, the kit comprising a panel of padlock probes, or a panel of sets of padlock probes as defined above, together with one or more components selected from:
(i) a restriction oligonucleotide capable of hybridizing to a RO sequence present in a padlock probe;
(ii) a restriction enzyme capable of cleaving the restriction cleavage site;
(iii) a ligase enzyme for circularization of a padlock probe;
(iv) a polymerase enzyme for performing a RCA reaction;
(v) one or more amplification primers for a RCA reaction or further amplification reaction;
(vi) nucleotides, buffers, and/or other reagents for performing a ligase and/or RCA and/or further amplification reaction;
(vii) reagents for detecting the amplification products of a RCA reaction or further amplification reaction.

As discussed above, the reagents for detection may include detection oligonucleotides, capture/array oligonucleotides, arrays or solid supports carrying array/capture oligonucleotides, and such like. They may further include other reaction components for the detection reaction. Detection oligonucleotides may be labelled in different ways, as discussed above. For example, they may be fluorescently or colorimetrically labelled. For the detection, further reagents may be required to generate a detectable signal, for example a developer reagent to generate a signal for colorimetric detection.

The invention will be further described in the following non-limiting Examples with reference to the drawings in which:

FIG. 1 shows an advantage of the present invention in reducing background signal in a multiplex padlock probe detection method. A: a padlock probe according to the prior art can hybridize to an RCA product and act as a primer for an extension reaction using the RCA product as an extension template. Cleavage of the extension product and circularization of the resulting monomers can incorporate the 'incorrect' analyte-specific reporter sequence into an RCA template, as described above. B: a padlock probe according to the present invention can hybridize to an RCA product and act as a primer for an extension reaction using the RCA product as an extension template. Cleavage of the extension product and circularization of the resulting monomers removes the 5' analyte-specific reporter sequence, and ensures it is not incorporated into an RCA template. Probes comprising 5' and 3' target-specific end sequences (5' ES and 3' ES), analyte-specific reporter sequences (A), restriction oligonucleotide sequences (R) and detection oligonucleotide sequences (D) are shown.

FIG. 2 shows a further advantage of the present invention in reducing background signal in a multiplex padlock probe detection method. FIG. 2A: a padlock probe according to the prior art can hybridize to an RCA product and act as a primer for an extension reaction using the RCA product as an extension template. Cleavage of the extension product can provide a monomer comprising the 'incorrect' analyte-specific reporter sequence that can be detected on a solid phase. FIG. 2B: a padlock probe according to the present invention can hybridize to an RCA product and act as a primer for an extension reaction using the RCA product as an extension template. Cleavage of the extension product removes the 5' analyte-specific reporter sequence, and ensures it is not detected on a solid phase. Probes comprising 5' and 3' target-specific end sequences (5' ES and 3' ES), analyte-specific reporter sequences (A), restriction oligonucleotide sequences (R) and detection oligonucleotide sequences (D) are shown.

FIG. 3 shows the background signal generated when pools of 90 padlock probes (either of the design according to the present invention, or according to the design of the prior art) are contacted with capture oligonucleotides complementary to target nucleic acid sequences, which are used to immobilise the target nucleic acid sequences during detection, and subjected to circle-to-circle amplification (C2CA) in the absence of target nucleic acid molecules for the padlock probes, but in the presence of positive control oligonucleotides.

Figure 4:
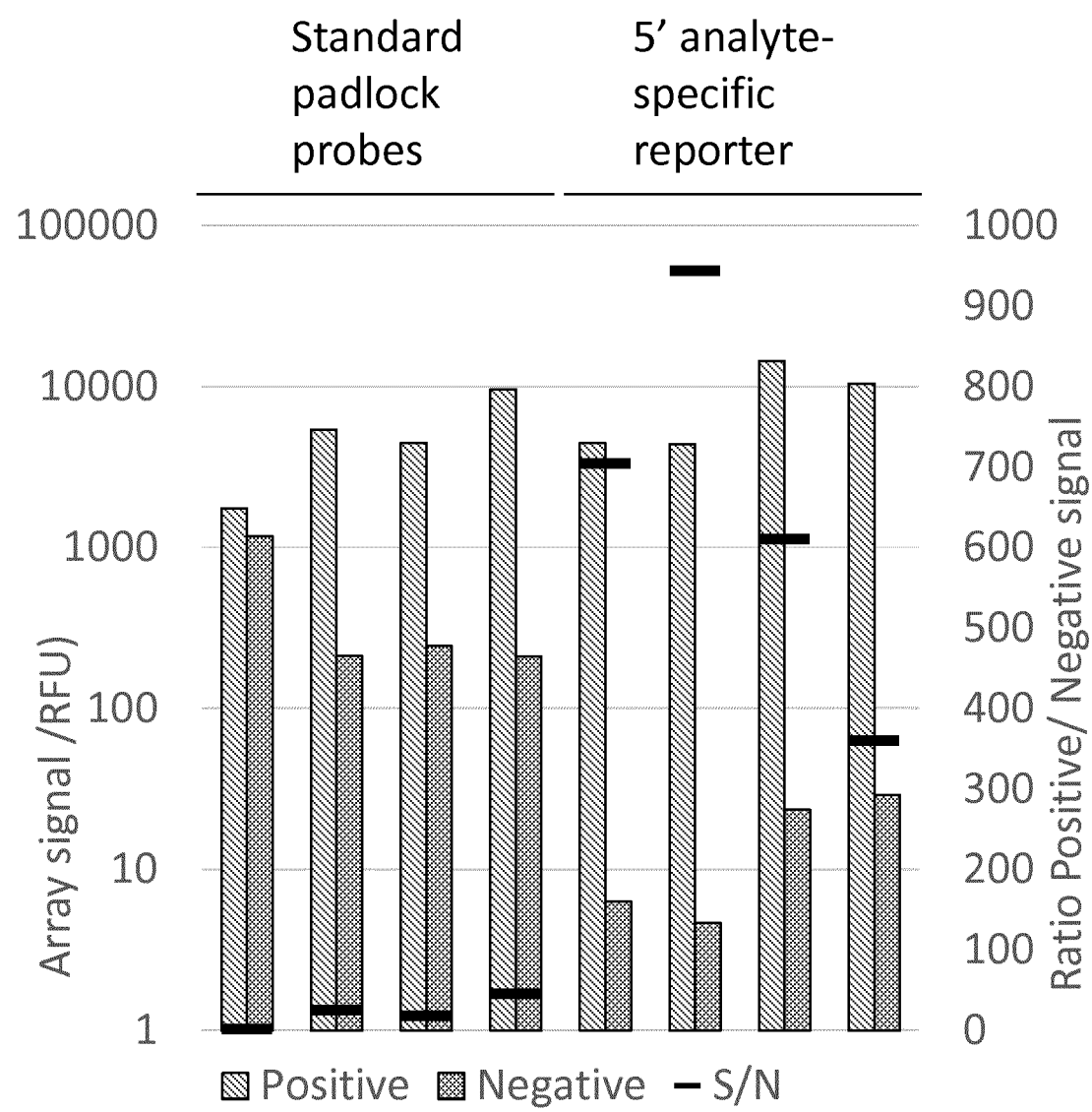
FIG. 4 shows signals generated for positive and negative control samples, and the signal/noise ratio for the multiplexed detection of *E. coli* genomic DNA.

FIG. 4 shows the signal generated for positive and negative control samples, and the signal/noise ratio for the multiplexed detection of E. coli genomic DNA. Pools of 90 padlock probes either of the design according to the present invention, or according to the design of the prior art were contacted with E. coli genomic DNA (positive), or no target nucleic acid sequence (negative), and subjected to circle-to-circle amplification (C2CA). Samples 1-4—detection was performed using padlock probes of the design according to the prior art. Sample 5-8—detection was performed using padlock probes according to the design of the present invention. The background signal generated in the negative control reactions was lower for the experiments performed using the padlock probes of the present invention than for the padlock probes of the design according to the prior art, and the signal-to-noise ratio (positive/negative) was higher, indicating a more sensitive detection method.

Figure 5:
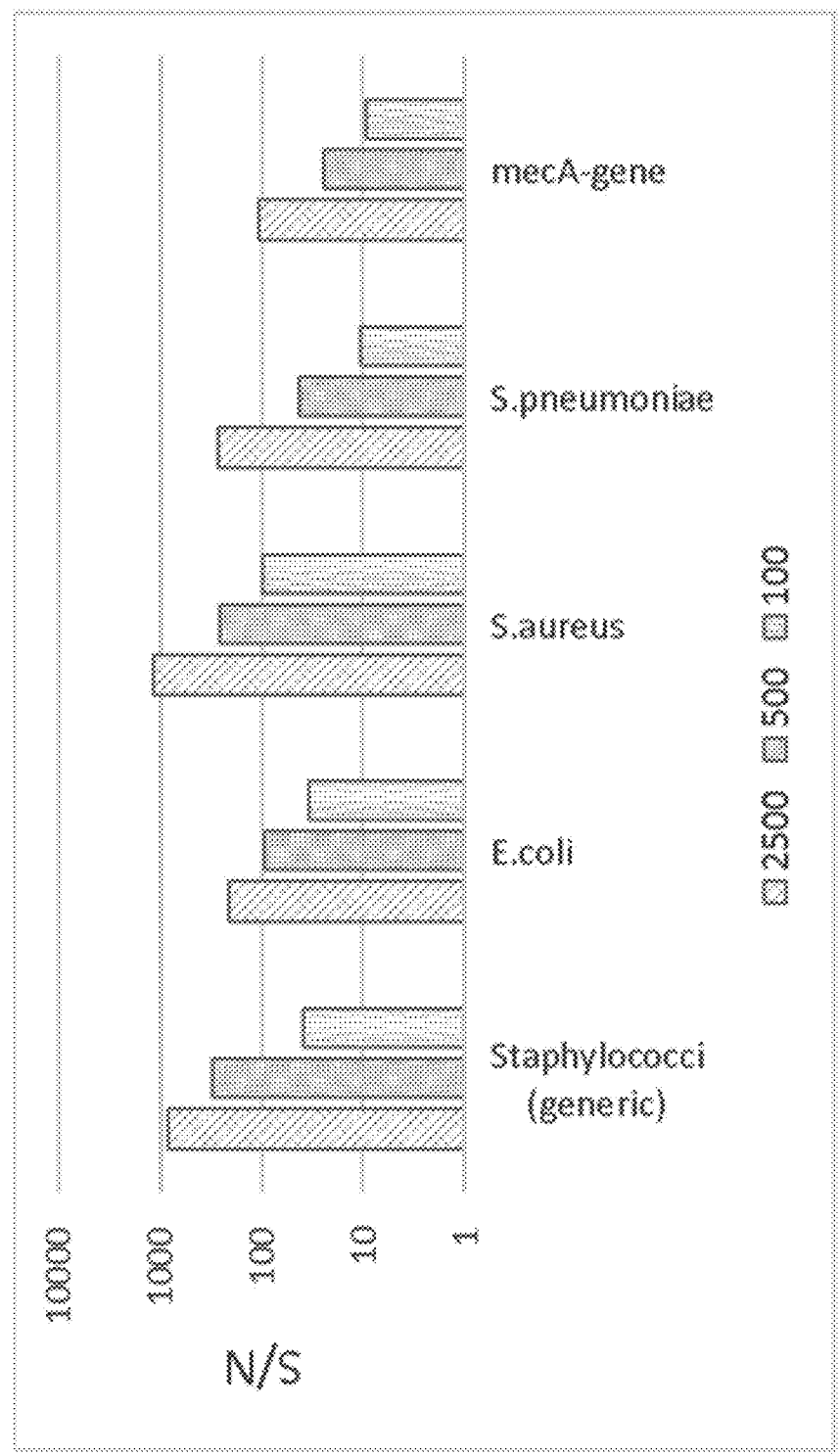
FIG. 5 shows signal-to-noise ratios for detecting DNA from different micro-organisms at different copy number values and for an antimicrobial resistance marker (mecA-gene), using probes with a combined RO/DO sequence.

FIG. 5 shows the signal-to-noise ratio for detecting DNA from a number of different micro-organisms at a number of different copy number values, as well as a well-known antimicrobial resistance marker (mecA-gene), using probes with a combined RO/DO sequence. A signal-to-noise ratio of between 10-100 was obtained for all samples at 100 copies of the target nucleic acid molecule.

FIGS. 6A and 6B show an advantage of the present invention in reducing background signal in a multiplex padlock probe detection method comprising HCRA. FIG. 6A: a padlock probe according to the prior art can hybridize to an RCA product and act as a primer for an extension reaction using the RCA product as an extension template. Amplification of the extension product using HRCA primers can amplify the 'incorrect' analyte-specific reporter sequence, as described above. FIG. 6B: a padlock probe according to the present invention can hybridize to an RCA product and act as a primer for an extension reaction using the RCA product as an extension template. Amplification of the extension product using HRCA primers ensures the incorrect 5' analyte-specific reporter sequence is not amplified and detected. Probes comprising 5' and 3' target-specific end sequences (5' ES and 3' ES), analyte-specific reporter sequences (A), first and second primer binding sites ($P_1$ and $P_2$) and detection oligonucleotide sequences (D) are shown.

Figure 7:
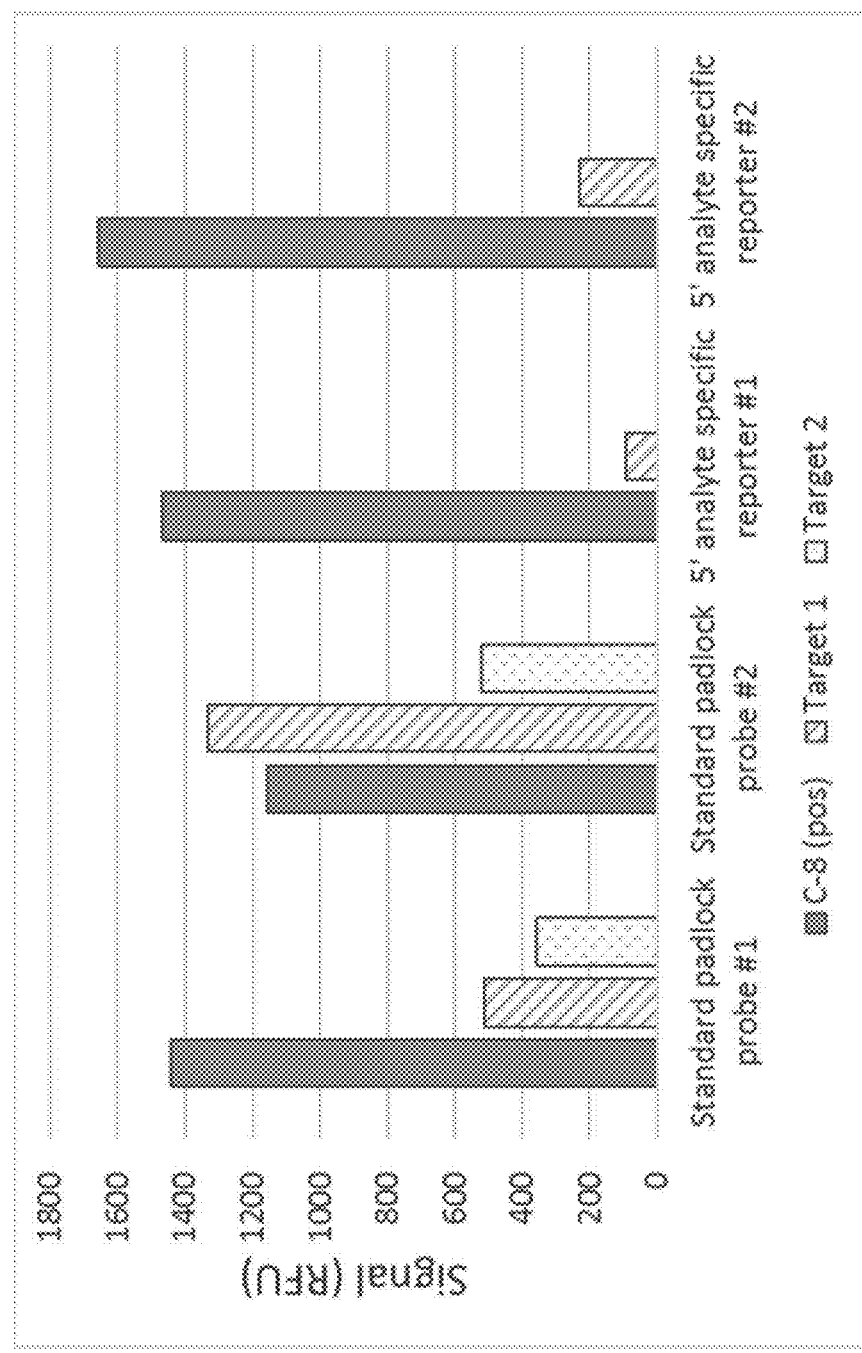
FIG. 7 shows signals for standard padlock probes and probes including 5' analyte specific reporter sequences.

FIG. 7 shows result from duplicate experiments (#1 and #2) for both standard padlock probes as well as probes comprising 5' analyte specific reporter sequences. The signal on the array from the positive control (C-8) is shown in grey, whereas the off-target signals from array features for Target 1 and 2 are shown in dashed and dotted bars respectively. The signal from these array features are from background amplification without presence of the correct target. Both standard padlock probes and 5' analyte specific reporters generated a signal for the positive control (C-8) whereas the background signal from the probes against targets 1 and 2, that were not present in the reaction is clearly larger when using standard padlock probes compared to 5' analyte specific reporters. (No signal detected against target 2 for 5' analyte specific reporters, 0-value in graph).

EXAMPLES

Example 1—Non-Template Dependent Signal Generated Using Padlock Probes

Non-template dependent signal in the assay was evaluated and compared to using a method as described in Göransson et al. 2012 PLoS One 7, e31068.

A multiplexed pool of 90 padlocks, complementary to different target nucleic acids in bacteria and yeast were used together with TE-buffer (10 mM Tris-HCl pH 7.5 1 mM EDTA); Dynabeads MyOne™ Streptavidin T1 beads (Invitrogen); a multiplexed pool of capture oligonucleotides complementary to a different part of the different target nucleic acids.

In each reaction, two positive control oligonucleotides are present: a linear padlock probe is added with a synthetic template as control for ligation and the RCA reaction; and a pre-formed circle as a control for the RCA reaction alone.

As no target nucleic acids are present in the sample no signal is expected, and any signal generated is background noise caused by non-specific between a padlock probes and another nucleic acid molecule (e.g. substrates formed from the positive control oligonucleotides). Two different concentrations of padlock probes were used, 10 nM and 100 nM.

Following contacting the capture oligonucleotides with the padlock probes, beads were washed once with 100 µl washing buffer containing 5 mM Tris-HCl (pH 7.5), 5 mM EDTA, 1 M NaCl, and 0.1% Tween-20. The elimination of excess linear padlock probes by washing reduces interference with the subsequent RCA reaction.

Circularized probes were amplified by C2CA, which includes serial enzymatic reactions starting with RCA. The RCA reaction was initiated by the addition of 20 µl ligation mixture containing 1× phi29 DNA polymerase buffer (Fermentas, Lithuania; 33 mM Tris-acetate (pH 7.9 at 37° C.), 10 mM Mg-acetate, 66 mM K-acetate, 0.1% (v/v) Tween-20, 1 mM DTT), 100 µM dNTPs, 0.2 µg/µl BSA, 25 nM primer, and phi29 DNA polymerase. The reaction was incubated at 37° C. for 15 min, and inactivated at 65° C. for 2 min. The RCA products were digested at 37° C. for 3 min by the addition of 3 units of AluI (New England Biolabs), 90 nM restriction oligonucleotide, 0.2 µg/µl BSA in 1× phi29 DNA polymerase buffer, and the reaction was terminated at 65° C. for 1 min. Ligation, amplification and labelling reactions were performed by the addition of a mixture containing 1.36 mM ATP, 100 µM dNTPs, 0.2 µg/µl BSA, 28 mU/µl T4 DNA ligase and 120 mU/µl phi29 DNA polymerase in 1× phi29 DNA polymerase buffer to a final volume of 50 µl. The reactions were incubated at 37° C. for 15 min, and terminated at 65° C. for 2 min. The above cleavage, ligation and amplification steps were repeated once. After the final RCA the product were digested once again into monomers to prepare the amplification products for analysis.

The digested sample was transferred to a microarray, incubated at 55° C. for 30 minutes followed by a wash with 1×SSC in RT. The hybridized RCA monomers is then labelled via hybridization of a detector oligo at 10 nM concentration in 2×SSC at 55° C. for 30 minutes, washed twice in 1×SSC at RT and spun dry.

The array was then scanned in an array scanner and the results analyzed using array image analysis software. The data recorded are the mean Relative Fluorescence Value from three replicate spots for a specific analyte-specific reporter sequence.

The positive control molecules provide RCA products which can act as substrates for subsequent primer extension reactions as described above. Background signal is also seen when only the pre-formed circle is added in the absence of ligase (data not shown).

The background signal generated using the padlock probes according to the design of the present invention was lower than for the padlock probes according to the design of the prior art (FIG. 3). Data shown are for a specific padlock probe according to the invention, and a padlock probe for the same target but designed according to the prior art methods. The data show a clear background reduction using the new method of the invention.

An exemplary sequence of a padlock probe for use in the above C2CA method is shown in below: [Underline is target specific sequences, bold sequence is restriction oligonucleotide (RO) sequence, Italics is Detection oligonucleotide (DO) sequence and lower case is the analyte-specific reporter (Array oligonucleotide (AO)) sequence.

```
Prior art method:
                                         (SEQ ID NO: 1)
5' P-CCTGGAACTGGCTGGTGCGTCTATTTAGTGGAGCCGACAGACCAG CTATCGTCGTaacctagtcgaggcgcttcaAGAGTGGGAAGCGAAAAT-

3'

New method:
                                         (SEQ ID NO: 2)
5' P-CCTGGAACTGGCTGGggatctcacgttctctggatTGCGTCTATT

TAGTGGAGCCGACAGACCAGCTATCGTCGTAGAGTGGGAAGCGAAAAT-

3'
```

Example 2—Analyte Detection

Signal to noise was evaluated and compared to using a method as described in Göransson et al. 2012 PLoS One 7, e31068.

The experiment was conducted as above, with 1250 copies of genomic *E. coli* DNA added to the positive reactions. Negative controls were performed as outlined above. The signal generated for each positive and negative reaction, and signal-to-noise values, are shown in FIG. 4.

The data show that the signal generated in the positive control samples using method of the present invention is equivalent to that of the prior art method, but that the signal generated in the negative control samples was lower (i.e. a reduced background) using the new method of the present invention.

It is noted that the negative control in the first experiment performed using the method of prior art had an unexpectedly high level of background signal. This indicates one of the effects the present method solves, i.e. unexpected high background in reactions.

Example 3—Combined RO/DO Sequence

Padlock probes with a separate array oligonucleotide sequence and a combined detection and restriction oligonucleotide sequence were used in the method as described above. In total, 90 padlock probes were used in the pool of padlock probes.

A sample spiked with genomic DNA preparations of four bacterial agents, one of which also contained the sequence for resistance gene mecA was analyzed at 2500, 500 or 100 genomic copies input amount, and the signal was compared to signal obtained in a negative control.

Signal-to-noise for each reaction was measured, and is shown in FIG. 5. A signal to noise between 10-100 was achieved at 100 genomic copies.

The background signal, reported as Relative Fluorescence Units (RFU) in the negative controls for the five padlock probes sets reported were 47. The average background signal for the remaining padlock probes in the reaction was 27 measured as RFU in all reactions, including were DNA were spiked in for the five padlock probe sets reported.

Short padlock probes are built up as below, exemplified with a padlock probe targeting the gram-negative bacteria *Pantoea agglomerans*: [Underline is target specific sequences; lower case is the analyte-specific reporter (Array oligonucleotide (AO)) sequence and bold sequence denotes the combined restriction and detection oligonucleotide (R/D O) sequence.

(SEQ ID NO: 3)
5' P-<u>AGGTCGTTAGAAAGCCC</u>gctgctaacaatgtgtcaacGACAGACC AGCTATCGTCGT<u>GGACCTAAACCTC</u>

Example 4—Non-Template Dependent Signal Generated Using Padlock Probes with HRCA Non-template dependent signal in an HRCA reaction was evaluated by running a reaction with a pre-ligated (circularized) probe, C-8 (see Table 1), together with a mix of standard padlock probes or padlock probes having 5' analyte specific reporter sequences. In one set of reactions standard padlock probes were used and in one set of reactions padlock probes having 5' analyte specific reporter sequences were used. The probes shown in the example were all present in 10 nM concentration.

The process was conducted as in Example 1 with the exception that instead of C2CA-step an HRCA reaction were run as follows:

Primers at 1 µM together with 500 µM dNTP:s with Uracil, 160 mU/µl BST pol v2 (New England Biolab)s and 0.2411 BSA run in 1× Isothermal Amp Buffer (New England Biolabs) at 65 C for 60 minutes.

After the HRCA the reaction were inactivated at 95° C. for 10 minutes, digested with added AluI restriction enzyme for 10 minutes before addition of fluorescent labelled detection oligo were made at 10 µM concentration, the reaction heated to 95° C. and added to an oligonucleotide array and allowed to cool down to 55° C. and incubated for a total of 60 minutes. Washing and imaging of the array as described in Example 1. The addition of detection oligonucleotide at high concentration was to compete out remaining primers from the reaction, as they have the same polarity and complementarity to the HRCA product to be detected, as the detection oligonucleotide.

In FIG. 7 the results from duplicate experiments (#1 and #2) for both standard padlock probes as well as 5' analyte specific reagents are shown. Probes according to the design of the present invention result in a greatly reduced background signal when used in conjunction with HRCA primers, when compared to standard padlock probes.

Sequences used in the experiment are shown in Table 1. [Underline is target binding sequences; lower case is the analyte-specific reporter (Array oligonucleotide (AO) sequence); bold sequences denote the detection oligonucleotide sequence and reverse primer sequence; and italic denotes the forward primer sequence.]

The Sequence Listing entitled 130457-03_ST25, created on Oct. 15, 2019, the size of the ASCII text file being 6,607 bytes, is hereby incorporated by reference in its entirety.

TABLE 1

| Standard padlock probes | | SEQ ID NO: | |
|---|---|---|---|
| QP-676 | Probe, C-8 (pos) | 4 | /5Phos/<u>AGATCACGAGCACAGAAA</u>TGCGTCTATTTAGTGGAG CCGACAGACCAGCTATCGTCGTatacagtggcagtagcacga<u>C GATAAACCTATCGACCCT</u> |
| QP-662 | Probe, target 1 | 5 | /5Phos/<u>CATACGACATCGTTGATCA</u>TGCGTCTATTTAGTGGA GCCGACAGACCAGCTATCGTCGTtaaggccctgcactgctgta<u>CAATCAGACTTACACTAGCC</u> |
| QP-663 | Probe, target 1 | 6 | /5Phos/<u>GGGAACGGTTCTTGGG</u>TGCGTCTATTTAGTGGAGCC GACAGACCAGCTATCGTCGTtaaggccctgcactgctgta<u>TAG GCTTAAAGGCCTAGTAA</u> |
| QP-739 | Probe, target 2 | 7 | /5Phos/<u>CGCCAGTTTCGAGTGA</u>TGCGTCTATTTAGTGGAGCC GACAGACCAGCTATCGTCGTtcgtacagagattgacctgc<u>GCC TATGACCTCGGGA</u> |
| QP-740 | Probe, target 2 | 8 | /5Phos/<u>ATGGTCAGCCGCAGTT</u>GCGTCTATTTAGTGGAGCCG ACAGACCAGCTATCGTCGTtcgtacagagattgacctgc<u>AGGG GCGCTGACTT</u> |

TABLE 1-continued

| Standard padlock probes | | SEQ ID NO: | |
|---|---|---|---|
| QP-741 | Probe, target 2 | 9 | /5Phos/<u>GGATCCAACACCTAGCAT</u>GCGTCTATTTAGTGGAGC<br>C*GACAGACCAGCTATCGTCGT*tcgtacagagattgacctgc<u>GC<br>ACTGAATCCCGGAAA</u> |
| Q-2132 | Primer + | 10 | GACAGACCAGCTATCGTCGT |
| Q-2282 | Primer − | 11 | GGCTCCACTAAATAGACGCA |
| 5' analyte specific reporter | | | |
| QP-1160 | Probe, target 1 | 12 | /5Phos/<u>CATACGACATCGTTGATCA</u>taaggccctgcactgct<br>gta*GACAGACCAGCTATCGTCGT*TGCGTCTATTTAGTGGAGCC<u>CAATCAGACTTACACTAGCC</u> |
| QP-1161 | Probe, target 1 | 13 | /5Phos/<u>GGGAACGGTTCTTGGG</u>taaggccctgcactgctgta<br>*GACAGACCAGCTATCGTCGT*TGCGTCTATTTAGTGGAGCC<u>TAG<br>GCTTAAAGGCCTAGTAA</u> |
| QP-1162 | Probe, target 2 | 14 | /5Phos/<u>CGCCAGTTTCGAGTGA</u>tcgtacagagattgacctgC<br>*GACAGACCAGCTATCGTCGT*TGCGTCTATTTAGTGGAGCC<u>GCC<br>TATGACCTCGGGA</u> |
| QP-1163 | Probe, target 2 | 15 | /5Phos/<u>ATGGTCAGCCGCAGTT</u>cgtacagagattgacctgC*G<br>AACAGCCAGCTATCGTCGT*TGCGTCTATTTAGTGGAGCC<u>AGGG<br>GCGCTGACTT</u> |
| QP-1164 | Probe, target 2 | 16 | /5Phos/<u>GGATCCAACACCTAGCA</u>tcgtacagagattgacctg<br>C*GACAGACCAGCTATCGTCGT*TGCGTCTATTTAGTGGAGCC<u>GC<br>ACTGAATCCCGGAAA</u> |
| QP-1166 | Probe C-8 (pos) | 17 | /5Phos/<u>AGATCACGAGCACAGAAA</u>atacagtggcagtagcac<br>ga*GACAGACCAGCTATCGTCGT*TGCGTCTATTTAGTGGAGCC<u>C<br>GATAAACCTATCGACCCT</u> |
| Q-2131 | Primer − | 18 | ACGACGATAGCTGGTCTGTC |
| Q-2281 | Primer + | 19 | TGCGTCTATTTAGTGGAGCC |
| Detection oligo (both systems) | | | |
| Q-1599 | Detection | 20 | 5'-Cy3-TGCGTCTATTTAGTGGAGCC |
| Template for positive control (C-8) | | | |
| Q-1064 | Template | 21 | TTTGAGGAAACCCGTCCTCCCGTCTATTTCGCTCCTCATATCG<br>TTCCAGCGCTTTTAGCACGTTTCTGTGCTCGTGATCTAGGGTC<br>GATAGGTTTATCGC |

The invention claimed is:

1. A multiplexed method of detecting an analyte in a sample using two or more padlock probes each specific to a different target sequence, each target sequence being either part of an analyte or indicative of the presence of an analyte in the sample, said method comprising:
   (a) contacting the sample with the two or more padlock probes and allowing each padlock probe of the two or more padlock probes to hybridize to its respective target sequence, if present;
   (b) circularizing any padlock probe which has hybridized to its target nucleic acid sequence by ligation to form a rolling circle amplification (RCA) template;
   (c) amplifying ligated padlock probes by performing at least a linear RCA reaction using the RCA template(s) formed in step (b) to form first rolling circle amplification product(s) (RCP), wherein a first RCP is a concatemer comprising monomers which are complementary to the circularized padlock probe which templated its formation, and optionally, simultaneously with or subsequently to said linear RCA reaction, performing a further amplification reaction to amplify the first RCP(s);
   (d) optionally, performing, during or after step (c), a restriction cleavage step to cleave any unligated padlock probes, or any non-specific extension products of unligated padlock probes, or any amplicons generated therefrom, and optionally to cleave the first RCP(s) or further amplification products thereof; and
   (e) detecting the RCP(s) of step (c), the further amplification product(s) of the RCP(s) of step (c) when step (c) includes performing the further amplification reaction to amplify the first RCP(s), or the cleaved monomers of the first RCP(s), or the further amplification products of step (d) to detect the analyte(s);
   wherein each padlock probe comprises:
   (i) 5' and 3' end sequences, wherein each end sequence is capable of hybridizing to a corresponding complementary site in the same target sequence, the target sequence being different for each padlock probe, such that upon said hybridization the ends of the padlock probe are brought into juxtaposition, directly or indirectly, for ligation to circularize the padlock probe, and between the said 5' and 3' end sequences;
   (ii) at least one reporter sequence, at least one of which reporter sequences is an analyte-specific reporter sequence; and
   (iii) at least one of:
      a restriction oligonucleotide (RO) sequence capable of hybridizing to a complementary sequence to create a restriction cleavage site, and
      a first amplification primer binding site for said further amplification reaction, when step (c) includes performing the further amplification reaction to amplify the first RCP(s),
   wherein any RO sequence in the probe is located 3' of the analyte-specific reporter sequence;
   and wherein where the padlock probe comprises an RO sequence the restriction cleavage of step (d) uses a restriction enzyme capable of cleaving the restriction cleavage site, optionally together with a restriction oligonucleotide which is complementary to and capable of hybridizing to the restriction oligonucleotide (RO) sequence, and cleavage at said restriction cleavage site occurs 3' of the analyte-specific reporter sequence, and where the padlock probe comprises a first amplification primer binding site for the further amplification reaction, it does not contain a second amplification primer binding site 5' of the analyte-specific reporter sequence.

2. The method of claim 1, wherein each padlock probe comprises, between its 5' and 3' ends, a said restriction oligonucleotide (RO) sequence and at least one reporter sequence, at least one of the reporter sequences being an analyte-specific reporter sequence, and said method comprises:
   (a) contacting the sample with the two or more padlock probes and allowing the probes to hybridize to their respective target sequences, if present;
   (b) circularizing any padlock probe which has hybridized to its target nucleic acid sequence by ligation to form a rolling circle amplification (RCA) template;
   (c) performing a RCA reaction which comprises at least a linear RCA reaction using the RCA template(s) formed in step (b) to form first rolling circle amplification product(s) (RCP), wherein a first RCP is a concatemer comprising monomers which are complementary to the circularized padlock probe which templated its formation;
   (d) during or after step (c), performing a restriction cleavage step using a restriction enzyme capable of cleaving the restriction cleavage site, optionally together with a restriction oligonucleotide which is complementary to and capable of hybridizing to the restriction oligonucleotide (RO) sequence; and
   (e) after step (d), detecting the amplification product(s) to detect the analyte(s), and optionally wherein the cleaved monomers are detected in step (e) to detect the analyte.

3. The method of claim 1, wherein:
   (i) the cleavage of step (d) results in cleavage of concatemeric RCPs into monomers and monomers are detected in step (e); and/or (ii) in restriction cleavage step (d) a restriction site for cleavage is created by hybridization of a restriction oligonucleotide to the RO sequence, and wherein the restriction oligonucleotide is added during or after any preceding step.

4. The method of claim 3, wherein in (ii), the restriction oligonucleotide hybridizes to the RCP at the sequence which is complementary to the RO sequence of the padlock probe, thereby creating a cleavage site in each monomer, and wherein the cleavage of step (d) results in cleavage of the concatemeric RCP into cleaved monomers.

5. The method of claim 3, wherein:
the monomers comprise the analyte-specific reporter sequence of the padlock probe which templated the formation of the first RCP, or its complement, and wherein detecting the amplification product comprises contacting the monomers with an oligonucleotide immobilized to a solid surface, wherein said oligonucleotide is capable of hybridizing to the analyte-specific reporter sequence or its complement.

6. The method of claim 1, wherein the restriction oligonucleotide (RO) sequence is a common RO sequence which is the same in all the padlock probes.

7. The method of claim 1, wherein (i) the method includes, simultaneously with or subsequently to said linear RCA reaction, performing the further amplification reaction to amplify the first RCP(s) to increase the number of monomers, and/or (ii) the restriction oligonucleotide is added in excess of that required to hybridize to the first RCP(s).

8. The method of claim 7, wherein said further amplification comprises:
(A) one or more rounds of a circle-to-circle amplification (C2CA) reaction, wherein the first RCP is monomerized and the monomers are ligated into secondary circles which are used as RCA templates in a second RCA reaction to generate a second RCP, which may optionally be monomerized, and optionally further subjected to a further round of C2CA to generate a third or further RCP, and optionally third or further generations of monomers; and/or
(B):
(i) if the first or previous RCP has not been monomerized, hybridizing the restriction oligonucleotide to the RCP at the sequence which is complementary or homologous to the RO sequence of the padlock probe, thereby to create a cleavage site in each monomer, and wherein the cleavage of step (d) results in cleavage of the concatemeric RCP into cleaved monomers,
(ii) allowing both ends of the monomers to hybridize to uncleaved restriction oligonucleotide, ligating the hybridized ends to circularize the monomers thereby forming a secondary RCA template and performing a second RCA reaction using said secondary RCA template to form a second RCA product; and
(iii) optionally repeating steps (i) and (ii) one or more times; and/or
(C) a first, second and third RCA reaction.

9. The method of claim 8, wherein in (A), the restriction oligonucleotide is used to template the ligation of monomers into circles, and optionally to prime the second, third and/or further RCA reaction.

10. The method of claim 1, wherein the RCA reaction of step (c) is a hyperbranched RCA (HRCA) reaction, wherein the linear RCA reaction takes place as part of the HRCA reaction and wherein said HRCA reaction takes place prior to step (d).

11. The method of claim 10, wherein said HRCA reaction comprises contacting the RCA template of step (b) with first and second HRCA amplification primers, wherein the first HRCA amplification primer is complementary and capable of hybridizing to a first portion of the RCA template of step (b), and wherein the second HRCA amplification primer is homologous to a second portion of the RCA template of step (b) and capable of hybridizing to a sequence which is complementary to said second portion, wherein the amplification primers are added before, during, or after step (b), and wherein double-stranded extension products are formed, comprising a first strand which is complementary to at least part of the first RCP and a second strand which is homologous to at least part of the first RCP, and optionally, wherein the extension products are cleaved into monomers and the cleaved monomers are detected in step (e).

12. The method of claim 1, wherein:
the method includes, simultaneously with or subsequently to said linear RCA reaction, performing a further amplification reaction to amplify the first RCP(s), the further amplification of the first RCP(s) being performed after step (d) by an amplification reaction which requires at least two primers, and optionally, wherein said further amplification reaction is a polymerase chain reaction (PCR), a loop-mediated isothermal amplification (LAMP), a strand displacement amplification (SDA), a helicase dependent amplification (HDA) or a Smart Amplification Process (SMAP); and/or
the analyte-specific reporter sequence is an array oligonucleotide (AO) sequence, wherein the array oligonucleotide sequence or its complement is capable of hybridizing to an array oligonucleotide in an array.

13. The method of claim 1, wherein:
(A) the analyte-specific reporter sequence is a detection oligonucleotide (DO) sequence wherein the detection oligonucleotide sequence or its complement is capable of hybridizing to an optionally labelled detection oligonucleotide and the hybridization of the detection oligonucleotide is detected to detect the amplification product; and/or
(B) the analyte-specific reporter sequence is or comprises an amplification primer binding site sequence wherein the amplification primer binding site sequence or its complement is capable of hybridizing to an amplification primer; and/or
(C) a reporter sequence is a detection oligonucleotide sequence (DO) and wherein the monomers comprise the detection oligonucleotide sequence or its complement, wherein detecting the amplification product comprises contacting the monomers with an optionally labelled detection oligonucleotide complementary to and capable of hybridizing to the detection oligonucleotide sequence or its complement, and detecting the hybridization of the detection oligonucleotide to the detection oligonucleotide sequence to detect the amplification product; and/or
(D) the padlock probe comprises an analyte-specific reporter sequence and at least one further reporter sequence.

14. The method of claim 13, wherein in (D):
the further reporter sequence is common to all the padlock probes; and/or wherein the analyte-specific reporter sequence is an array oligonucleotide sequence or wherein the analyte-specific reporter sequence or its complement is capable of hybridizing to an oligonucleotide immobilized on a solid surface, and the further reporter sequence is a detection oligonucleotide sequence; and/or wherein the analyte-specific reporter sequence and at least one further reporter sequence are on opposite sides of the restriction oligonucleotide (RO) sequence, such that they are separated upon cleavage.

15. The method of claim 13, wherein in (D), the padlock probe comprises in the order 5' to 3':
   (i) an array oligonucleotide sequence (AO)-restriction oligonucleotide sequence (RO)-detection oligonucleotide (DO) sequence; or
   (ii) an array oligonucleotide sequence (AO)-restriction/detection sequence (RO/DO); or
   (iii) an array oligonucleotide sequence (AO)-detection oligonucleotide sequence (DO)-restriction oligonucleotide sequence (RO)—.

16. The method of claim 1, wherein a further reporter sequence is at least partially comprised within, or overlaps, the restriction oligonucleotide sequence, and optionally, wherein a detection oligonucleotide sequence is part of the restriction oligonucleotide sequence.

17. The method of claim 1, wherein:
   said first amplification primer binding site, when present is located 3' or within the analyte-specific reporter sequence; and/or
   the further amplification reaction, when included in step (c) comprises the use of at least a forward and a reverse amplification primer; and/or
   the further amplification reaction, when included in step (c) is PCR or a variant thereof, SDA, HDA, LAMP or SMAP; and/or
   the padlock probe further comprises a second amplification primer binding site for the further amplification reaction, and wherein the first and second amplification primer binding sites for the further amplification reaction are at least partially complementary to one another; and/or
   the padlock probe comprises distinct first and second amplification primer binding sites for the further amplification reaction, when included in step (c), wherein the second amplification primer binding site in the probe is homologous to the second amplification primer and the second amplification primer hybridizes to a sequence complementary to the second amplification primer, and optionally, wherein the two or more padlock probes each have a different first amplification primer binding site.

18. The method of claim 1, wherein the padlock probe comprises at least a first amplification primer binding site for a further amplification reaction and optionally an RO sequence, and said method comprises:
   (a) contacting the sample with the two or more padlock probes and allowing the probes to hybridize to their respective target sequences, if present;
   (b) circularizing any padlock probe which has hybridized to its target nucleic acid sequence by ligation to form a rolling circle amplification (RCA) template;
   (c) performing a linear RCA reaction using the RCA template(s) formed in step (b) to form first rolling circle amplification product(s) (RCP), wherein a first RCP is a concatemer comprising monomers which are complementary to the circularized padlock probe which templated its formation;
   (d) optionally performing a restriction cleavage step during or after step (c), using a restriction enzyme capable of cleaving the restriction cleavage site, optionally together with a restriction oligonucleotide which is complementary to and capable of hybridizing to the restriction oligonucleotide (RO) sequence, to cleave the concatemeric first RCPs into cleaved monomers; and
   (e) subjecting the first RCP of step (c) or the cleaved monomers of the first RCP from step (d) to a further amplification reaction using at least first and second amplification primers; and
   (f) detecting the RCP(s) of step (c), the further amplification product(s) of the RCP(s) of step (c), or the restriction cleavage product(s) of step (d) to detect the analyte(s);
   and optionally, following step (c) or step (d), the first RCP(s) or monomeric cleavage products thereof are separated into aliquots and step (e) is performed on the separate aliquots.

19. The method of claim 1, wherein the first amplification primer binding site is present and is located 3' of the analyte-specific reporter sequence.

* * * * *